United States Patent
Kawka et al.

(10) Patent No.: US 9,636,262 B2
(45) Date of Patent: May 2, 2017

(54) METHOD AND APPARATUS FOR TRANSFERRING A DISCRETE SUBSTRATE

(71) Applicant: The Procter & Gamble Company, Cincinnati, OH (US)

(72) Inventors: Paul Anthony Kawka, Kelso Township, IN (US); Bradley Edward Walsh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 17 days.

(21) Appl. No.: 14/747,118

(22) Filed: Jun. 23, 2015

(65) Prior Publication Data

US 2015/0374556 A1 Dec. 31, 2015

Related U.S. Application Data

(60) Provisional application No. 62/017,293, filed on Jun. 26, 2014.

(51) Int. Cl.
*B65G 53/66* (2006.01)
*A61F 13/15* (2006.01)
*B65G 37/00* (2006.01)
*B65G 43/08* (2006.01)
*B65G 51/03* (2006.01)

(52) U.S. Cl.
CPC ........ *A61F 13/15764* (2013.01); *B65G 37/00* (2013.01); *B65G 43/08* (2013.01); *B65G 51/035* (2013.01); *B65G 2811/0673* (2013.01); *B65G 2812/16* (2013.01)

(58) Field of Classification Search
CPC .. B65G 51/035; B65H 5/228; A61F 13/15764

USPC ..................... 406/12, 88; 271/195
See application file for complete search history.

(56) References Cited

U.S. PATENT DOCUMENTS

| 3,105,720 A | 10/1963 | Barker |
| 3,160,443 A | 12/1964 | Harris et al. |
| 3,437,335 A * | 4/1969 | Gluskin ................. F15C 1/001 271/195 |

(Continued)

FOREIGN PATENT DOCUMENTS

EP   2 491 906 A1   8/2012

OTHER PUBLICATIONS

PCT/US2015/037113 International Search Report, dated Sep. 23, 2015, 9 pages.

*Primary Examiner* — William R Harp
(74) *Attorney, Agent, or Firm* — Sarah M. DeCristofaro

(57) ABSTRACT

An apparatus and method for transferring a discrete substrate. A transfer apparatus may include a top plate and a bottom plate. The top plate and the bottom plate may include a first inboard supply port and a first outboard supply port and may define a passageway. The discrete substrate may enter the passageway at a first velocity and exit the passageway at a final velocity. The final velocity may be greater than the first velocity. A first inboard control valve and a first outboard control valve may be activated, and each valve may operate on a valve frequency that defines an on-period and an off-period for each cycle. Each cycle may be controlled by a controller. A visual detection device may track the discrete substrate and communicate with the controller. The discrete substrate may be adjusted as it advances in a machine direction.

37 Claims, 13 Drawing Sheets

(56) References Cited

U.S. PATENT DOCUMENTS

| | | |
|---|---|---|
| 3,503,607 A | 3/1970 | Gluskin |
| 3,747,922 A | 7/1973 | Groeber |
| 3,848,594 A | 11/1974 | Buell |
| 3,860,003 A | 1/1975 | Buell |
| 4,004,349 A | 1/1977 | Neumann |
| 4,131,320 A | 12/1978 | Volat et al. |
| 4,135,767 A | 1/1979 | Hench et al. |
| 4,210,801 A | 7/1980 | Gomez et al. |
| 4,451,182 A | 5/1984 | Lenhart |
| 1,493,548 A | 1/1985 | Ateya |
| 4,521,130 A | 6/1985 | Lenhart |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 1,834,735 A | 5/1989 | Alemany et al. |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,915,547 A | 4/1990 | Cahill et al. |
| 4,946,527 A | 8/1990 | Battrell |
| 5,037,244 A | 8/1991 | Newton |
| 5,151,092 A | 9/1992 | Buell et al. |
| 5,209,387 A | 5/1993 | Long et al. |
| 5,221,274 A | 6/1993 | Buell et al. |
| 5,417,524 A | 5/1995 | Newton |
| 5,484,237 A | 1/1996 | Langenbeck |
| 5,562,646 A | 10/1996 | Goldman et al. |
| 5,564,441 A | 10/1996 | Sharp et al. |
| 5,599,335 A | 2/1997 | Goldman et al. |
| 5,628,097 A | 5/1997 | Benson et al. |
| 5,634,636 A * | 6/1997 | Jackson ............... B65H 5/228 271/184 |
| 5,669,894 A | 9/1997 | Goldman et al. |
| 5,916,661 A | 6/1999 | Benson et al. |
| 5,951,006 A | 9/1999 | Biegelsen et al. |
| 6,027,112 A * | 2/2000 | Guenther ............... B65G 51/03 271/194 |
| 6,032,923 A * | 3/2000 | Biegelsen ............. B65H 5/228 137/599.07 |
| 6,039,316 A * | 3/2000 | Jackson ................ B65H 5/066 271/194 |
| 6,107,539 A | 8/2000 | Palumbo et al. |
| 6,305,772 B1 * | 10/2001 | Berkoben ........... B41J 2/16552 347/34 |
| 6,494,646 B1 | 12/2002 | Sala |
| 6,505,483 B1 | 1/2003 | Hoetzl et al. |
| 6,545,197 B1 | 4/2003 | Muller et al. |
| 6,790,798 B1 | 9/2004 | Suzuki et al. |
| 7,513,716 B2 | 4/2009 | Hayashi et al. |
| 7,569,039 B2 | 8/2009 | Matsuda et al. |
| 7,861,846 B1 * | 1/2011 | Salditch ............. B65G 47/1457 198/392 |
| 8,092,143 B2 | 1/2012 | Yang et al. |
| 8,292,549 B2 | 10/2012 | Iida |
| 2003/0131943 A1 * | 7/2003 | Frederisy .......... A61F 13/15617 156/538 |
| 2004/0097895 A1 | 5/2004 | Busam et al. |
| 2004/0158212 A1 | 8/2004 | Ponomarenko et al. |
| 2005/0107764 A1 | 5/2005 | Matsuda et al. |
| 2007/0090188 A1 * | 4/2007 | Li .......................... B65H 5/228 235/449 |
| 2009/0312730 A1 | 12/2009 | LaVon et al. |
| 2012/0061015 A1 | 3/2012 | LaVon et al. |
| 2012/0061016 A1 | 3/2012 | LaVon et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2014/0110052 A1 | 4/2014 | Findley et al. |

* cited by examiner

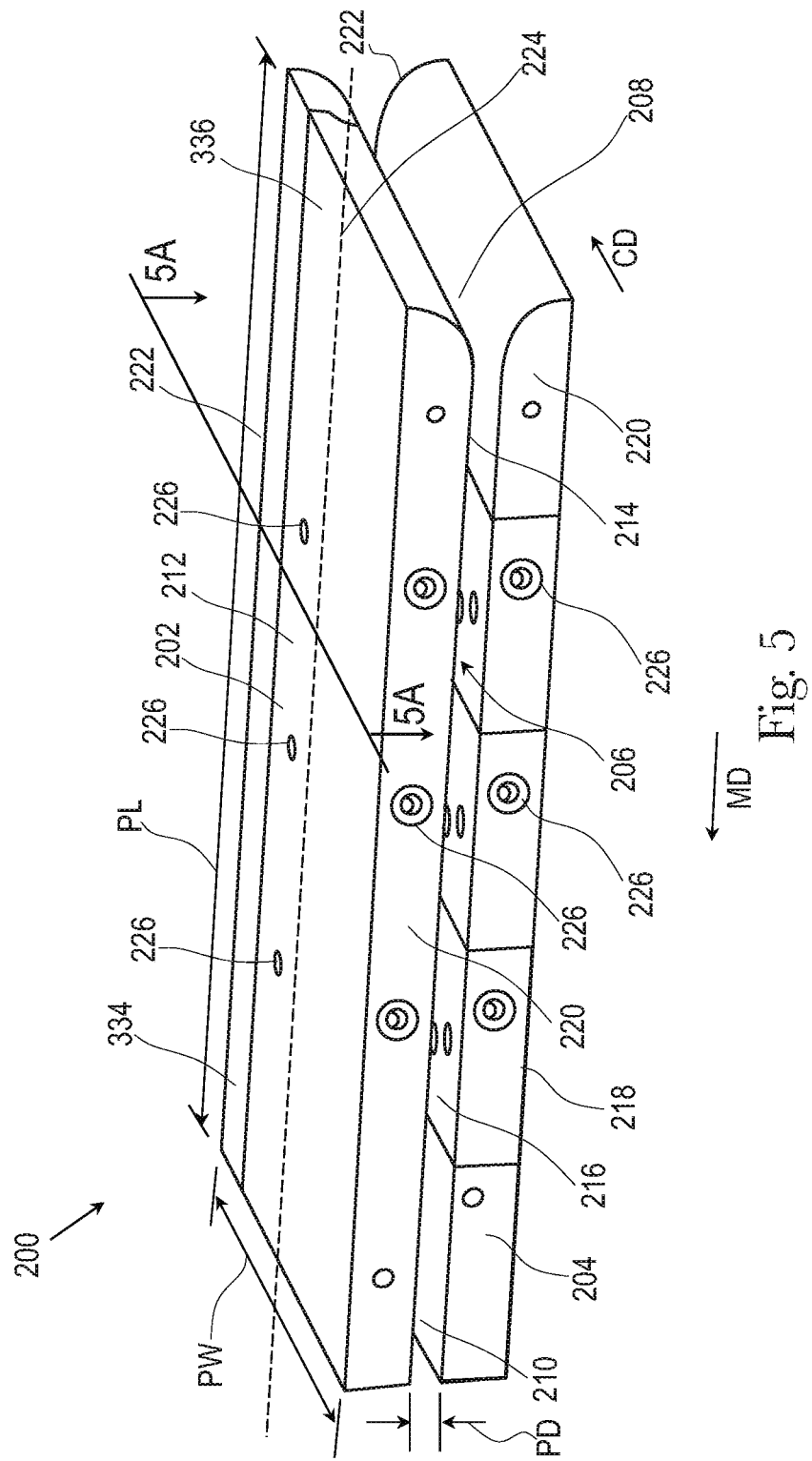

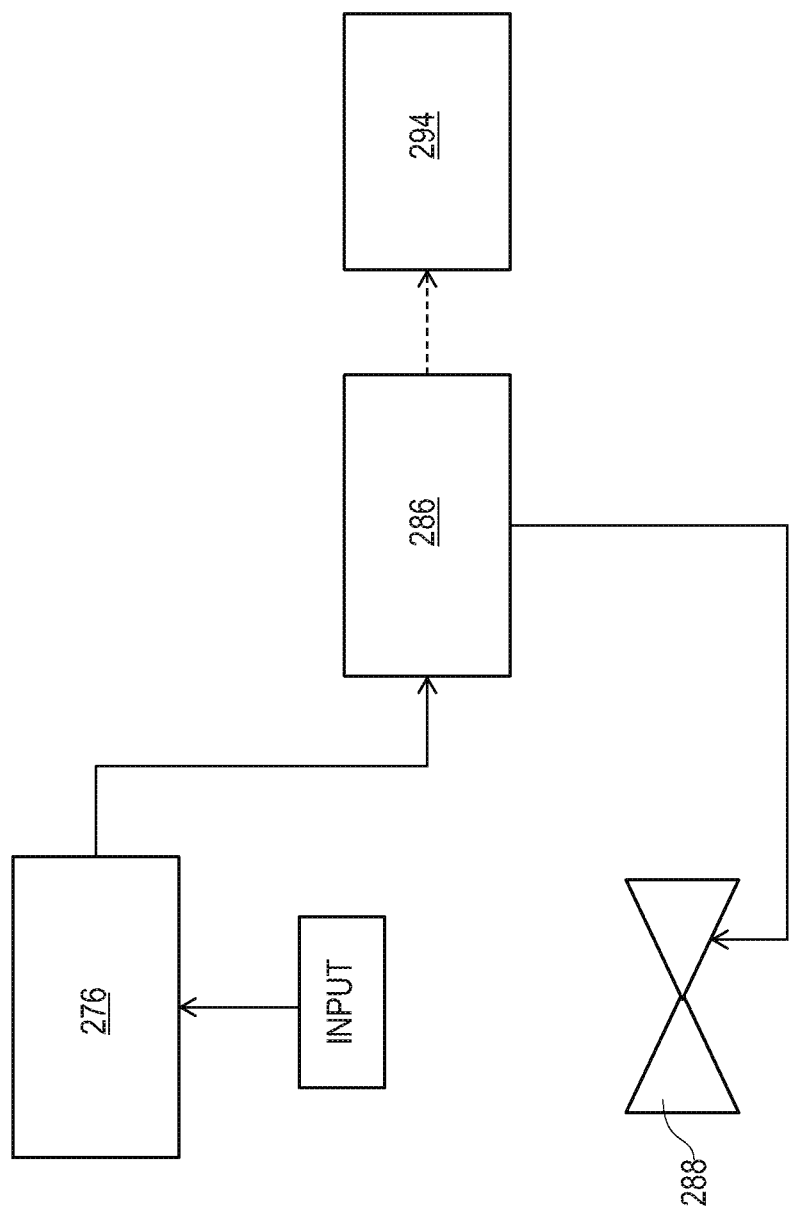

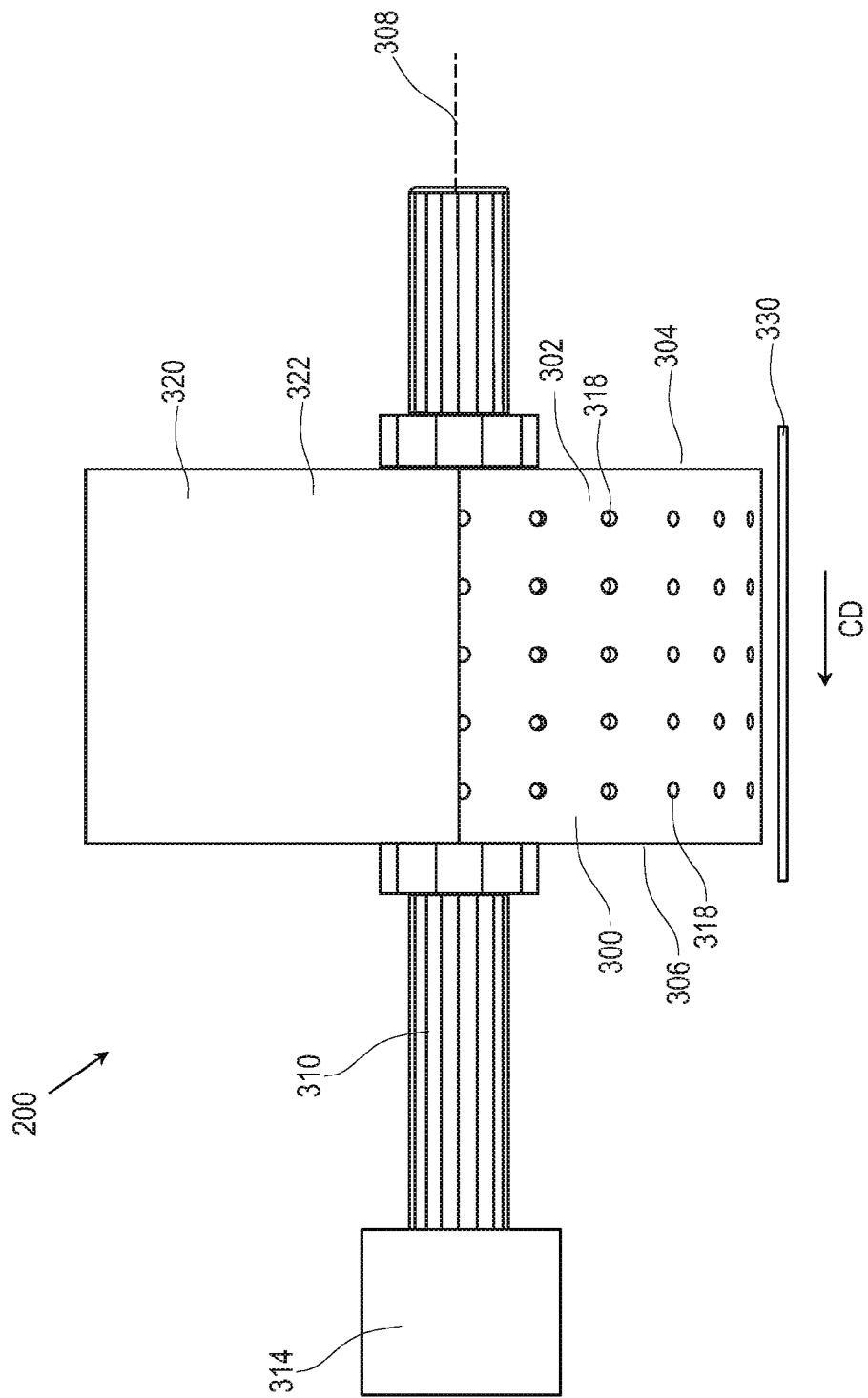

METHOD AND APPARATUS FOR TRANSFERRING A DISCRETE SUBSTRATE

CROSS REFERENCE TO RELATED APPLICATIONS

This application claims the benefit, under 35 USC 119(e), to U.S. Provisional Patent Application No. 62/017,293 filed on Jun. 26, 2014, which is herein incorporated by reference in its entirety.

FIELD OF THE INVENTION

The present disclosure relates to apparatuses and methods for manufacturing absorbent articles, and more particularly, apparatuses and methods for transferring a discrete substrate.

BACKGROUND OF THE INVENTION

Along an assembly line, diapers and various types of other absorbent articles may be assembled by adding components to and otherwise modifying an advancing, continuous substrate of material. For example, in some processes, advancing substrates of material are combined with other advancing substrates of material. In other examples, individual components created from advancing substrates of material are combined with advancing substrates of material, which in turn, are then combined with other advancing substrates of material. Substrates of material and component parts used to manufacture diapers may include: backsheets, topsheets, absorbent cores, front and/or back ears, fastener components, and various other types of substrates and components such as leg elastics, barrier leg cuff elastics, and waist elastics. Once the desired component parts are assembled, the advancing substrate(s) and component parts are subjected to a final knife cut to separate the substrate(s) into discrete diapers or other absorbent articles. The discrete diapers or absorbent articles may also then be folded and packaged.

As mentioned above, during the assembly process, advancing substrates of material may be combined with component parts and other advancing substrates of material to form absorbent articles. Generally, component parts may be manufactured separate from other advancing substrates on a manufacturing line. For example, a continuous substrate of material may be used to form back ears and/or front ears. Further, additional components may be added to these back ears and/or front ears prior to being added to another advancing substrate of material. To add these component parts to an advancing substrate, the component parts must be positioned correctly so that they may be laid down on the advancing substrates in a desired orientation with respect to the advancing substrate. Further, the velocity of the component parts must substantially match that of the velocity of the advancing substrate so that the component parts are placed in the desired position on the advancing substrates. Nonetheless, due the structure of these component parts, which may be irregularly shaped or disproportionately weighted, and the limitations of currently available manufacturing equipment, manufacturers are limited as to how fast the advancing substrates can progress. The advancing substrate can only advance at a speed that the currently available manufacturing equipment can precisely deliver and position the component part onto the advancing substrate. However, due to increased demand for products and, thus, a necessity to speed up the manufacturing process, a need exists for improved apparatuses and methods of manufacturing absorbent articles that include transferring and positioning a discrete substrate on an advancing substrate.

SUMMARY OF THE INVENTION

Aspects of the present disclosure relate to an apparatus and method for assembling absorbent articles. The transfer apparatus may include a top plate and a bottom plate opposite the top plate. The top plate and the bottom plate include a first inboard supply port, a first inboard injector port fluidly connected to the first inboard supply port, a first outboard supply port adjacent to the first inboard supply port, and a first outboard injector port fluidly connected to the first outboard supply port. The top plate and the bottom plate may also define a passageway having an entry portion and an exit portion. The transfer apparatus may also include a first inboard control valve and a first outboard control valve. The first inboard control valve may be operatively connected to the first inboard supply port. The first inboard control valve may regulate a flow of a fluid to the first inboard supply port and the first inboard injector port. The first outboard control valve may be operatively connected to the first outboard supply port. The first outboard control valve may regulate the flow of the fluid to the first outboard supply port and the first outboard injector port. A visual detection device positioned adjacent to at least one of the top plate and the bottom plate such that at least a portion of at least one of a first surface and a second surface of a discrete substrate is detectable by the visual detection device. A controller may be operatively connected to the visual detection device and at least one of the first inboard control valve and the first outboard control valve. The discrete substrate may enter through the entry portion of the passageway at a first velocity, move through the passageway in a machine direction, and exit through the exit portion of the passageway at a final velocity. The final velocity may be greater than the first velocity.

In another embodiment, a method for transferring a discrete substrate may include the following steps: providing a transfer apparatus comprising a top plate and a bottom plate opposite the top plate, wherein the top plate and the bottom plate include a first inboard supply port, and a first outboard supply port adjacent to the first inboard supply port, and wherein the top plate and the bottom plate define a passageway having an entry portion, an exit portion opposite the entry portion, and a central longitudinal axis extending in a machine direction; feeding a discrete substrate comprising a leading edge portion, a trailing edge portion opposite the leading edge portion, a central portion between the leading edge portion and the trailing edge portion, a first surface, and a second surface opposite the first surface through the transfer apparatus, wherein the discrete substrate enters through the entry portion of the passageway at a first velocity and exits through the exit portion of the passageway at a final velocity, wherein the final velocity is greater than the first velocity; activating a first inboard control valve to supply fluid to the first inboard supply port; activating a first outboard control valve to supply fluid to the first outboard supply port, wherein the first inboard control valve and the first outboard control valve operate on a valve frequency, wherein the valve frequency defines an on-period and an off-period for each cycle; controlling each of the first inboard control valve and the first outboard control valve with a controller, wherein the controller modifies the on-period and the off-period for each cycle for each of the first inboard control valve and the first outboard control valve;

advancing the discrete substrate in a machine direction; tracking at least a portion of the discrete substrate with a visual detection device, wherein the visual detection device is positioned adjacent to at least one of the top plate and the bottom plate such that at least a portion of at least one of the first surface and the second surface of the discrete substrate is detectable by the visual detection device; and adjusting the discrete substrate.

BRIEF DESCRIPTION OF THE DRAWINGS

FIG. 5 is a perspective view of a transfer apparatus in accordance with one non-limiting embodiment of the present disclosure;

FIG. 8 is a schematic representation of communication between elements of a transfer apparatus in accordance with one non-limiting embodiment of the present disclosure;

FIG. 10B is a front view of a transfer apparatus in accordance with one non-limiting embodiment of the present disclosure;

DETAILED DESCRIPTION OF THE INVENTION

Figure 1:
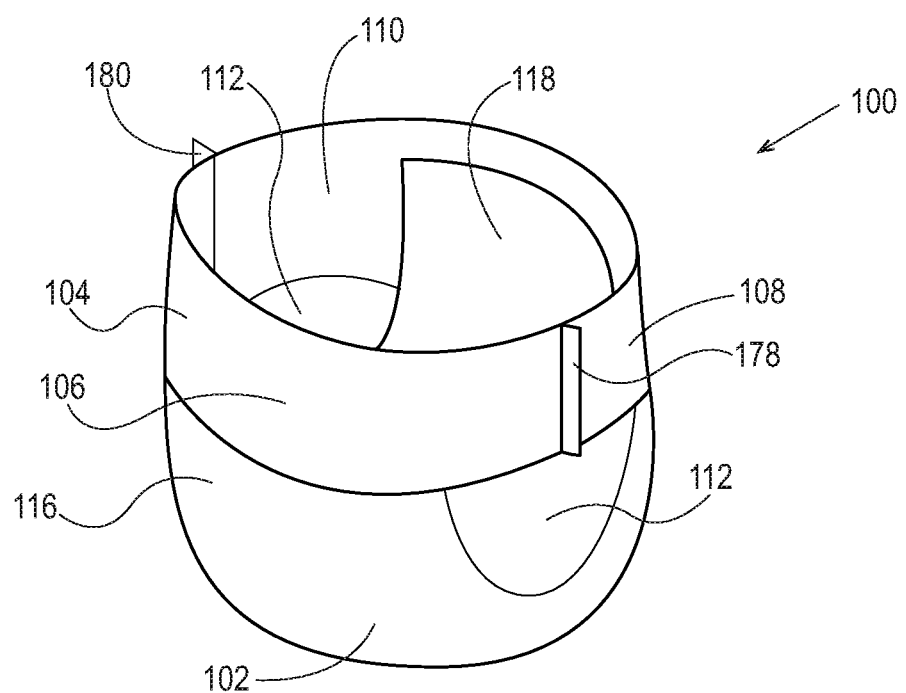
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant may be configured with a continuous or closed waist opening and at least one continuous, closed, leg opening prior to the article being applied to the wearer.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a material made from continuous (long) filaments (fibers) and/or discontinuous (short) filaments (fibers) by processes such as spunbonding, melt-blowing, carding, and the like. Nonwovens do not have a woven or knitted filament pattern.

The term "machine direction" (MD) is used herein to refer to the direction of material flow through a process. In addition, relative placement and movement of material may be described as flowing in the machine direction through a process from upstream in the process to downstream in the process.

The term "cross direction" (CD) is used to herein refer to the direction perpendicular to the direction of material flow through a process. The cross direction may be substantially perpendicular to the machine direction.

The terms "inboard" and "outboard" are used herein to refer to a positional relationship between the structure modified by these terms with respect to one another and not with respect to a centerline or an axis. In this manner, the terms are being used simply to identify a first position, and a second position that is different or opposite the first position.

The present disclosure relates to apparatuses and methods for manufacturing absorbent articles. More particularly, the apparatuses and methods are directed to transferring and positioning a discrete substrate on an advancing substrate.

As discussed in more detail below, the apparatuses and methods according to the present disclosure may be utilized in the production of various components of absorbent articles, such as diapers. To help provide additional context to the subsequent discussion of the process embodiments, the following provides a general description of absorbent articles in the form of diapers that include components including the materials that may be used by the methods and apparatuses discussed herein.

Figures 2, 3A, 3B:
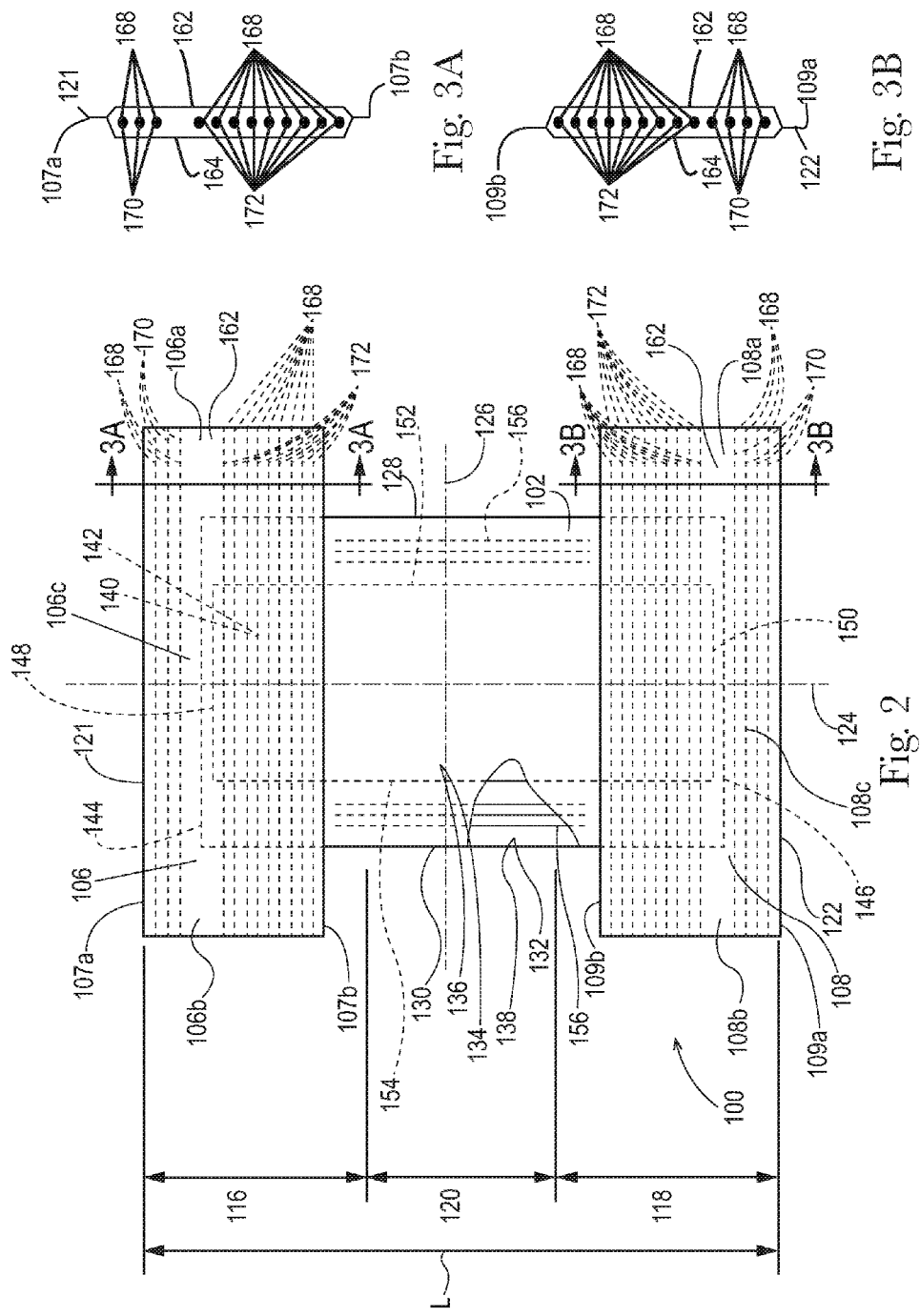
FIG. 2 is a partially cut away plan view of the diaper pant shown in FIG. 1.
FIG. 3A is a cross-sectional view of the diaper pant of FIG. 2 taken along line 3A-3A in accordance with one non-limiting embodiment of the present disclosure.
FIG. 3B is a cross-sectional view of the diaper pant of FIG. 2 taken along line 3B-3B in accordance with one non-limiting embodiment of the present disclosure.
Figure 4:
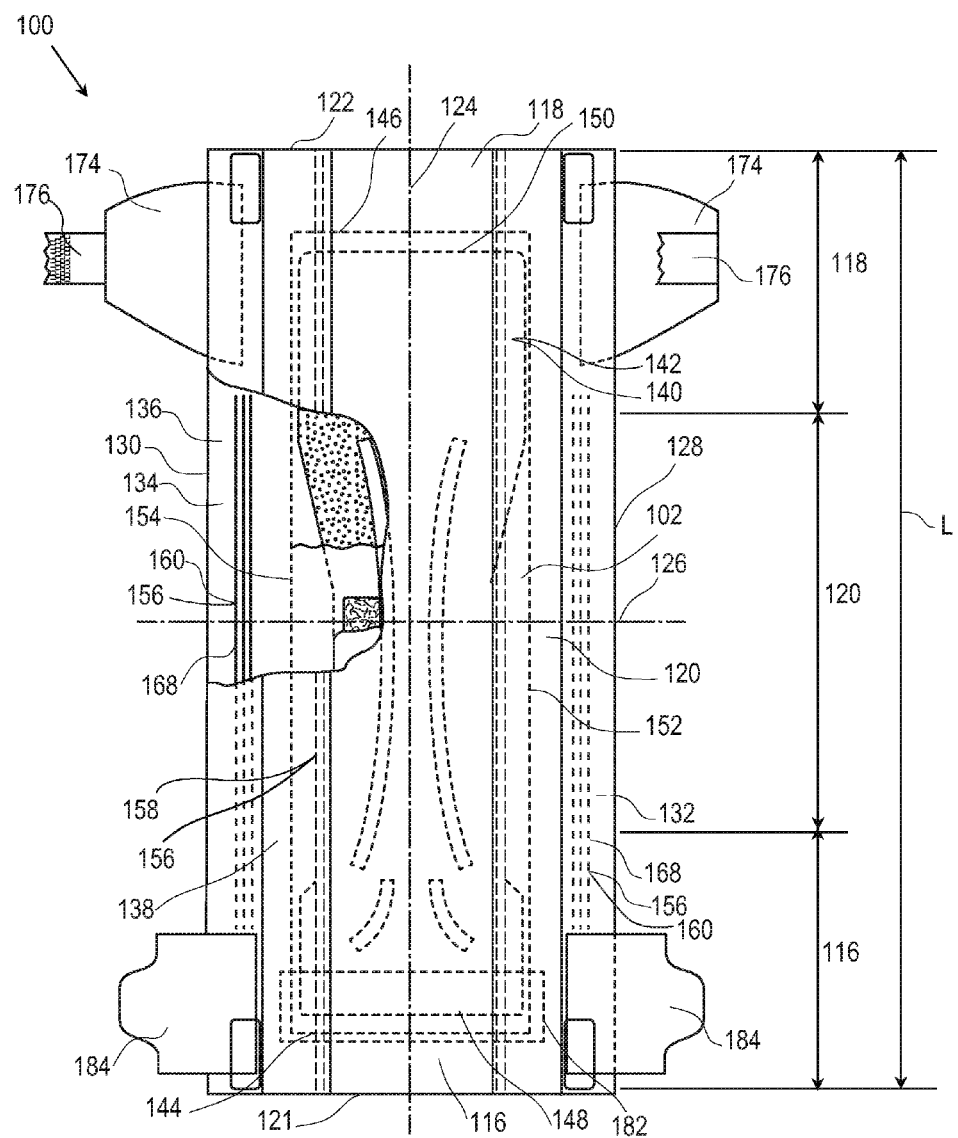
FIG. 4 is a partially cut away plan view of a diaper in accordance with one non-limiting embodiment of the present disclosure.

FIGS. 1, 2, and 4 illustrate an example of an absorbent article 100, such as a diaper, that may be assembled with the apparatuses and methods discussed herein. In particular, FIG. 1 shows a perspective view of an absorbent article 100 in a pre-fastened configuration, and FIG. 2 shows a plan view of the absorbent article 100 with the portion of the diaper that faces away from a wearer oriented towards the viewer. The absorbent article 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the absorbent article 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1, 2 and 4, the absorbent article 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the absorbent article 100 may also include other features, such as leg elastics and/or leg cuffs to enhance the fit around the legs of the wearer.

The periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. When the absorbent article 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. Moreover, the crotch region 120 may be generally positioned between the legs of the wearer with the absorbent core 142 extending from the front waist region 116 through the crotch region 120 to the back waist region 118.

It is also to be appreciated that a portion or the whole of the absorbent article 100 may also be made laterally extensible. The additional extensibility may help allow the absorbent article 100 to conform to the body of a wearer during movement by the wearer. The additional extensibility may also help, for example, allow the diaper 100, including a chassis 102 having a particular size before extension, to extend in the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also include a woven or nonwoven material, polymeric films such as thermoplastic films of polyethylene or polypropylene, and/ or a multi-layer or composite materials comprising a film and a nonwoven material (e.g., having an inner film layer and an outer nonwoven layer). The backsheet may also include an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the absorbent article 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets, and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

The absorbent article 100 may also include an absorbent assembly 140 that is joined to the chassis 102. As shown in FIGS. 2 and 4, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core may comprise a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

The absorbent article 100 may also include elasticized leg cuffs 156. It is to be appreciated that the leg cuffs 156 may be and are sometimes also referred to as leg bands, side flaps, barrier cuffs, elastic cuffs, or gasketing cuffs. The elasticized leg cuffs 156 may be configured in various ways to help reduce the leakage of body exudates in the leg regions. For example, in some embodiments, a gasketing leg cuff 160 may be positioned adjacent to the side edge 130, 128 of the chassis 102 and a barrier leg cuff 158 may be positioned between a gasketing leg cuff 160 and the longitudinal axis 124 of the absorbent article 100. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. Patent Publication No. 2013/0255865A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, the absorbent article may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic belt 108 defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

Referring to FIG. 4, in some embodiments, the absorbent article 100 may include a fastening system. The fastening system can be used to provide lateral tensions about the circumference of the absorbent article to hold the absorbent article on the wearer. The fastening system may comprise a fastener such as tape tabs, hook and loop fastening components, interlocking fasteners such as tabs and slots, buckles, buttons, snaps, and/or hermaphroditic fastening components. A landing zone 182 may be provided on the front waist region 116 for at least a portion of the fastener to be releasably attached to. Exemplary fastening systems may include those described in U.S. Pat. Nos. 3,848,594; 4,662, 875; 4,846,815; 4,894,060; 4,946,527; 5,151,092; and 5,221,274.

As illustrated in FIG. 4, the absorbent article 100 may comprise front ears 184 and back ears 174. The front ears 184 and the back ears 174 may be an integral part of the chassis 102. For example, the front ears 184 and the back ears 174 may be formed from the topsheet 138 and/or the backsheet 136. Alternatively, the front ears 184 and the back ears 174 may be attached to the backsheet 136 and/or the topsheet 138. The front ears 184 and the back ears 174 may be extensible to facilitate attachment on the landing zone 182 and to maintain placement around the waist of the wearer. The back ears 174 may comprise a tab member 176. The tab member 176 may be attached to a portion of the back ears 174 to facilitate attachment to the landing zone 182.

As previously mentioned, the apparatuses and methods according to the present disclosure may be utilized to assemble discrete absorbent articles 100 and/or various components of absorbent articles 100, such as for example, chassis 102, elastic belts 106, 108, leg cuffs 156, back ears 174, and/or front ears 184. Although the following methods may be provided in the context of absorbent articles 100, as shown in FIGS. 1, 2, and 4, it is to be appreciated that the methods and apparatuses herein may be used with various process configurations and/or absorbent articles, such as for example, disclosed in U.S. Pat. No. 7,569,039; U.S. Patent Publication Nos. 2005/0107764A1; 2012/0061016A1; 2012/0061015A1; 2013/0255861A1; 2013/0255862A1; 2013/0255863A1; 2013/0255864A1; and 2013/0255865A1.

FIG. 5 shows an exemplary schematic representation of a transfer apparatus that may be used in the manufacture of an absorbent article 100, as previously described. More specifically, the transfer apparatus 200 may be used to transfer and adjust the position and the velocity of a discrete substrate. Velocity referred to herein encompasses both longitudinal velocity, or the velocity parallel to the machine direction, and angular velocity. The folding apparatus 200 may include a top plate 202 and a bottom plate 204, opposite the top plate 202. The top plate 202 and the bottom plate 204 may define a passageway 206 therebetween. The passageway 206 may extend in a machine direction MD. The top plate 202 and the bottom plate 204 may include one or more supply ports that may be configured to release a fluid into the passageway 206. The discrete substrate may be fed into the passageway 206 at an entry portion 208. One or more control valves may be used to control the supply ports and, in turn, direct the discrete substrate using fluid from the entry portion 208 to an exit portion 210 of the passageway. At the exit portion 210, the discrete substrate may be oriented in a desired position and advancing at a desired velocity, such that the discrete substrate may be disposed on an advancing substrate. The aforementioned will be discussed in more detail herein.

As illustrated in FIG. 5, the transfer apparatus 200 may include a top plate 202 and a bottom plate 204. The top plate 202 may include a first external surface 212 and a first internal surface 214. The bottom plate 204 may include a second internal surface 216 and a second external surface 218. The first internal surface 214 of the top plate 202 may be in facing relationship with the second internal surface 216 of the bottom plate 204. The first internal surface 214 of the top plate 202 and the second internal surface 216 of the bottom plate 204 define a passageway 206 including an entry portion 208 and an exit portion 210. The first internal surface 214 of the top plate 202 and the second internal surface 216 of the bottom plate 204 may be separated by a plate distance PD. The plate distance PD may be determined by the properties of the discrete substrate, such as weight, rigidity, and dimensions, that is to pass between the top and bottom plate, and the amount of fluid flow required to more the discrete substrate through the passageway 206. In some embodiments, the plate distance PD may be from about 20 mm to about 1 mm and/or from about 10 mm to about 3 mm and/or from about 8 mm to about 6 mm, including all 0.5 mm therebetween.

Each of the top plate 202 and the bottom plate 204 may have a plate width PW that may extend in the cross direction CD. The plate width PW may be determined, in part, by the width of the discrete substrate that is to be transported along the passageway 206. The plate width PW may be determined to be from about 5% to about 25% greater than the width of the discrete substrate to be transported along the passageway 206. In some example embodiments, the plate width PW may be from about 500 mm to about 5 mm and/or from about 400 mm to about 10 mm and/or from about 300 mm to about 25 mm. Further, each of the top plate 202 and the bottom plate 204 may have a plate length PL that extends in the machine direction MD. The plate length PL may be determined by the change in velocity that the discrete substrate is desired to undergo during transport from the entry portion 208 to the exit portion 210 of the passageway 206. In some example embodiments, the plate length Pl may be at least as long as the length of the discrete substrate, which extends in the machine direction MD.

Each of the top plate 202 and the bottom plate 204 may include an inboard side surface 220 and an outboard side surface 222, as shown in FIG. 5. Each of the inboard side surface 220 and the outboard side surface 222 may extend in a direction substantially parallel to the machine direction MD. The transfer apparatus 200 may also include a central longitudinal axis extending 224 in the machine direction MD and positioned between at least one of the inboard side surface 220 and the outboard side surface 222. Further, the top plate 202 and the bottom plate 204 may include a supply port 226. The supply port 226 may be defined by at least one of the first external surface 212 of the top plate 202, the second external surface 218 of the bottom plate 204, inboard supply surface 220 of the top plate 204 and the bottom plate 206, and the outboard supply surface 222 of the top plate 204 and the bottom plate 206. The supply ports 226 may be positioned along the central longitudinal axis 224 such that the passageway 206 may be supplied a fluid along the entire plate length PL. The supply ports may have any shape that allows fluid to be supplied to the passageway 206. For example, as shown in FIG. 5, the supply ports may have a substantially circular cross section. In some embodiments, for instance, the supply ports may have any one of a substantially rectangular, triangular, elliptical, or octagonal cross section.

Figure 5A:
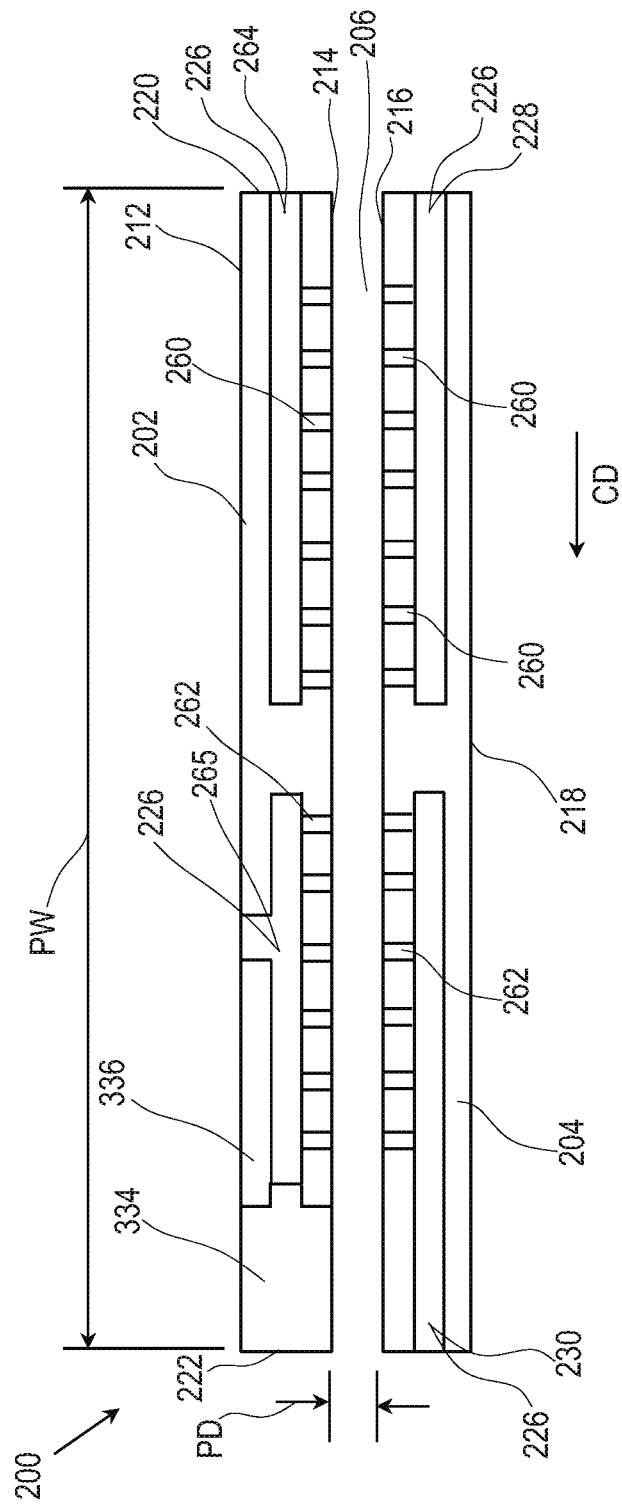
FIG. 5A is an end view of a transfer apparatus of FIG. 5 taken along line 5A-5A in accordance with one non-limiting embodiment of the present disclosure.

More specifically, as illustrated in FIG. 5A, the transfer apparatus 200 may include a first inboard supply port 228 and a first outboard supply port 230 defined by the bottom plate 204. Further, the transfer apparatus may include a first upper inboard supply port 264 and a first upper outboard supply port 265. Each inboard and outboard supply port may include one or more inboard 260 and outboard 262 injection ports, respectively, as will be discussed in detail herein. It is to be appreciated that the plate width PW and/or the width of the discrete substrate 240 may be used to determine the number of supply ports and injector ports. For example, the plate width PW may be small enough such that an inboard supply port and an outboard supply port each include a single injector port. In some other embodiments, the plate width may be large enough such that an inboard supply port and an outboard supply port each include more than one injector port. The transfer apparatus 200 may also include either an inboard supply port that extends across the central longitudinal axis or an outboard supply port that extends across the central longitudinal axis. The transfer apparatus 200 may be configured such that the supply port extends from the outboard supply surface or the inboard supply surface.

Figure 6:
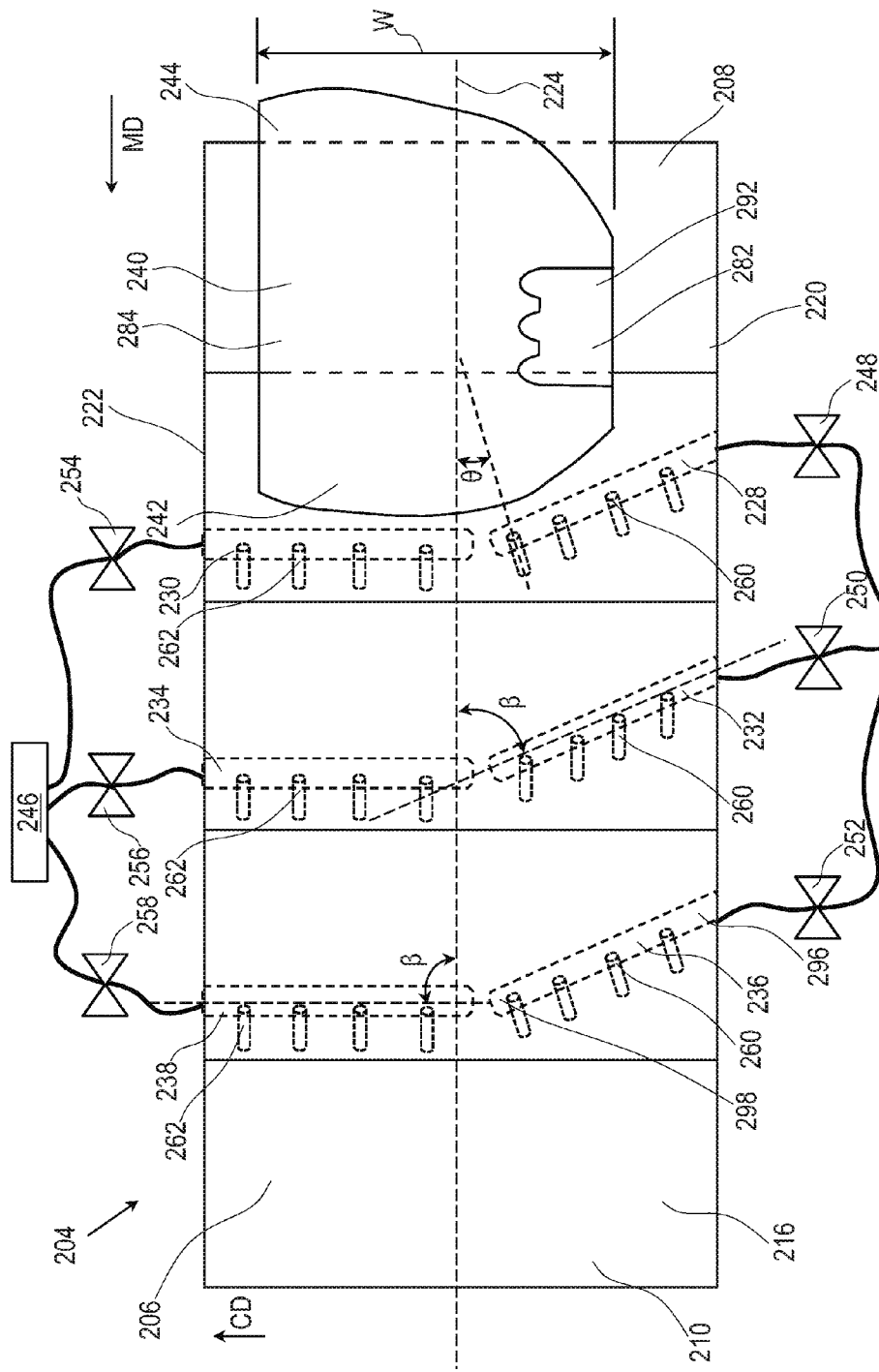
FIG. 6 is a top view of a bottom plate of a transfer apparatus in accordance with one non-limiting embodiment of the present disclosure.

In some embodiments, the top plate 202 and the bottom plate 204 may include a plurality of supply ports. For example, as illustrated in FIG. 6, the bottom plate 204 may include a first inboard supply port 228, a first outboard supply port 230, a second inboard supply port 232, a second outboard supply port 234, a third inboard supply port 236, and a third outboard supply port 238. It is to be appreciated that a transfer apparatus 200 may include any number of supply ports that would allow the discrete substrate to be transferred at a desired velocity and positioned to be disposed on an advancing substrate. Each of the inboard supply ports may be positioned substantially parallel one another and each of the outboard supply ports may be positioned substantially parallel to one another. In some embodiments, each of the inboard supply ports may extend from the inboard supply surface 220 toward the central longitudinal axis 224. Each of the outboard supply ports may extend from the outboard supply surface 222 toward the central longitudinal axis 224. Each of the inboard supply ports and the outboard supply ports may include an inlet portion 296 and an end portion 298, opposite the inlet portion 296. The inboard supply ports and the outboard supply ports may be configured to accept fluid at the inlet portion 296 and to allow the fluid to move toward the end portion(s) 298.

It is to be appreciated that the inboard supply ports and the outboard supply ports may extend from the external surface of the top plate 202 or the bottom plate 204 and extend toward the passageway 206. It is also to be appreciated that each of the inboard supply ports do not have to be substantially parallel to one another and, in some embodiments, each of the inboard supply ports may be at an angle with respect to another inboard supply port. Similarly, each of the outboard supply ports may also be at an angle with respect to another outboard supply port.

Still referring to FIG. 6, each of the inboard supply ports and the outboard supply ports may be oriented at a supply port angle $\beta$. The supply port angle $\beta$ is the angle of the supply port with respect to the central longitudinal axis 224. The supply port angle $\beta$ may be from about 10 degrees to about 145 degrees and/or from about 20 degrees to about 105 degrees and/or from about 30 degrees to about 90 degrees. The supply port angle $\beta$ for each supply port may be determined by the profile of the discrete substrate 240. The discrete substrate 240 may include a leading edge portion 242 and a trailing edge portion 244, opposite the leading edge portion 242. Each of the leading edge portion 242 and the trailing edge portion 244 may have a profile. For example, as shown in FIG. 6, the discrete substrate 240 has a leading edge portion 242 that has a non-uniform curved profile. Thus, the supply ports may be oriented with respect to the central longitudinal axis 244 to substantially mirror the profile of the leading edge portion 242. It is believed that orienting the supply ports to substantially mirror the profile of the leading edge potion 242 allows the fluid discharged into the passageway to substantially engage the leading edge portion 242 of the discrete substrate 240 and to continue to advance the discrete substrate 240 in the machine direction MD.

Each inboard supply port may be fluidly connected with a fluid source 246. The supply of fluid from the fluid source 246 to each of the supply ports may be controlled by a control valve. A control valve may be any device that regulates the flow of fluid. For example, a control valve may be used to restrict and/or terminate the flow of fluid. As illustrated in FIG. 6, a first inboard control valve 248 may be positioned between the fluid source 246 and the first inboard supply port 228. Thus, the first inboard control valve 248 may control the flow of fluid to the first inboard supply port 228. Similarly, a second inboard control valve 250 may be positioned between the fluid source 246 and the second inboard supply port 232 and a third inboard control valve 252 may be positioned between the fluid source 246 and the third inboard supply port 236. The second inboard control valve 250 may control the flow of fluid to the second inboard supply port 232 and the third inboard control valve 252 may control the flow of fluid to the third inboard supply port 236.

Each outboard supply port may also be fluidly connected to a fluid source 246. It is to be appreciated that the inboard supply ports and the outboard supply ports may be connected with the same fluid source or a different fluid source. As illustrated in FIG. 6, a first outboard control valve 254 may be positioned between the fluid source 246 and the first outboard supply port 230. Thus, the first outboard control valve 254 may control the flow of fluid to the first outboard supply port 230. Similarly, a second outboard control valve 256 may be positioned between the fluid source 246 and the second outboard supply port 234, and a third outboard control valve 258 may be positioned between the fluid source 246 and the third outboard supply port 238. The second outboard control valve 256 may control the flow of fluid to the second outboard supply port 234 and the third outboard control valve 258 may control the flow of fluid to the third outboard supply port 238.

Each of the inboard control valves and the outboard control valves may be fast switching valves. Exemplary fast switching control valves are available from Festo of Hauppauge, N.Y. Further, different types of valves may be used, such as solenoid valves or piezo-electric valves. The inboard control valves and the outboard control valves may be operate on a valve frequency, which will be discussed in detail herein. Generally, the valve frequency relates to how much many times the control valve can cycle on and off over a certain period of time. For high-speed manufacturing, it is desired to have an inboard control valve and an outboard control valve having a valve frequency of greater than or equal to about 200 Hz or about 300 Hz or about 400 Hz or about 500 Hz or about 600 Hz. For clarity of explanation, the apparatuses and methods will be described as including an inboard control valve and an outboard control valve having a frequency of 500 Hz. However, it is to be appreciated that control valve may have a different valve frequency.

Each of the inboard supply ports and the outboard supply ports may include an injector port. The inboard injector port 260 and the outboard injector port 262 may transport a fluid from the inboard supply ports and the outboard supply ports, respectively, and into the passageway 206. Each of the inboard supply ports and the outboard supply ports may include any number of injector ports as needed to create the desired fluid flow within the passageway and to transport the discrete substrate at a desired velocity and in a desired position. Each of the injector ports may have a substantially circular cross section, as illustrated in FIG. 6. However, in some embodiments, the injector ports may have a non-circular cross section. For instance, the injector ports may have any one of a substantially rectangular, triangular, elliptical, or octagonal cross section.

For example, as illustrated in FIG. 6, each of the first inboard supply port 228, the second inboard supply port 232, and the third inboard supply port 236 may include four inboard injector ports 260. Each of the first outboard supply port 230, the second outboard supply port 234, and the third outboard supply port 238 include five outboard injector ports 262. The number of inboard injector ports may be greater than, less than, or equal to the number of outboard injector ports. The inboard injector ports included on an inboard supply port and the outboard injector ports included on an outboard supply port may be evenly spaced along the length of the inboard supply port. It is to be appreciated that the inboard injector ports and the outboard injector ports may also be non-uniformly spaced along the length of each of the inboard supply ports and the outboard supply ports. The inboard injector ports and the outboard injector ports may be spaced along the length such they may be non-uniformly spaced but rather spaced based on the properties of the discrete substrate such as weight distribution, material, and the profile of the leading edge portion.

Figure 7:
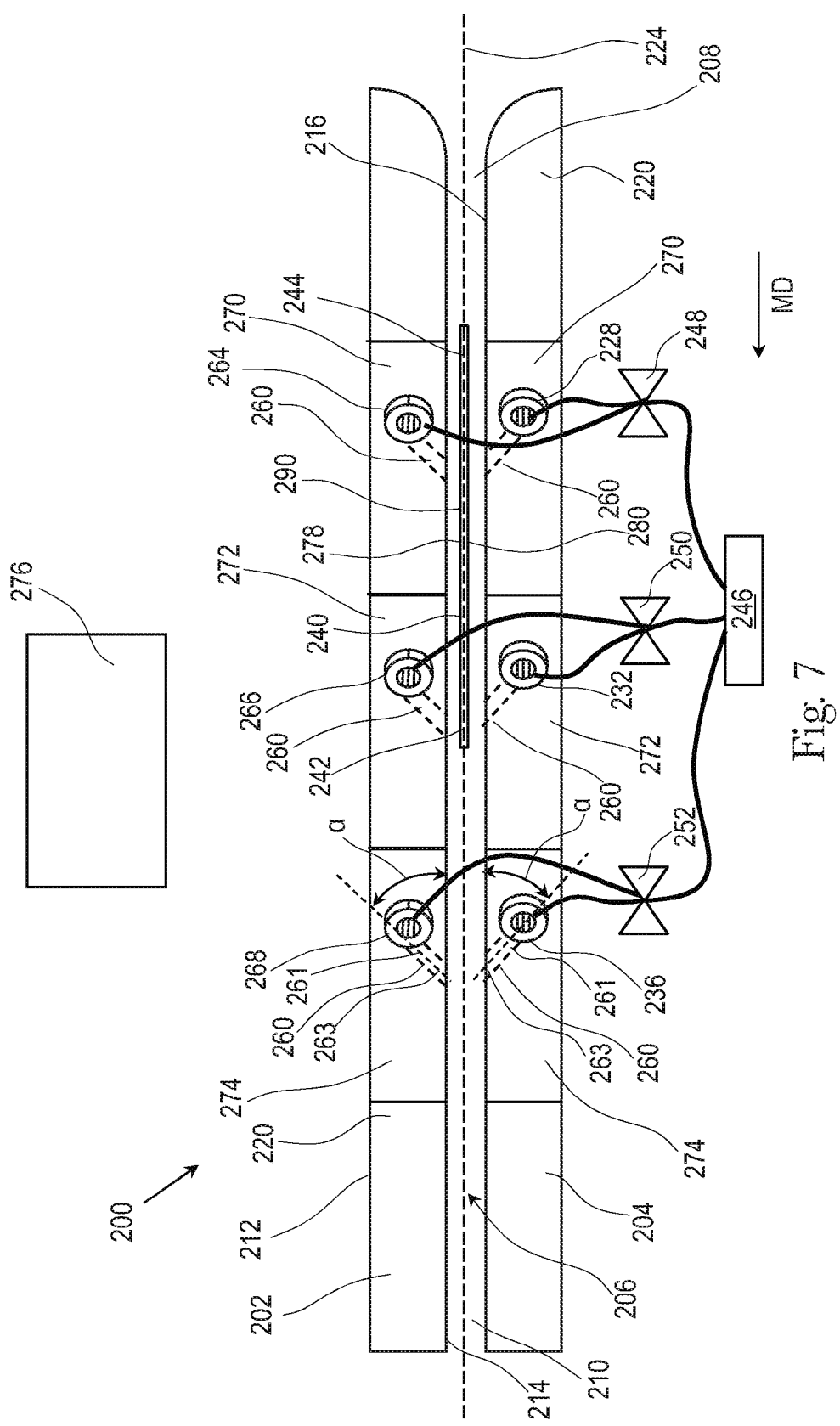
FIG. 7 is a side view of a transfer apparatus in accordance with one non-limiting embodiment of the present disclosure.

As illustrated in FIGS. 6 and 7, each inboard supply port may include an inboard injector port 260 that extends from a portion of the inboard supply port toward the passageway 206. Similarly, each outboard supply port may include an outboard injector port 262 that extends from a portion of the outboard supply port toward the passageway 206. Each of the inboard injector ports 260 and the outboard injector ports 262 may include a proximal end portion 261 adjacent to the inboard supply port and the outboard supply port, respectively, and a distal end portion 263, opposite the proximal end portion. Each of the inboard injector ports 260 and the outboard injector ports 262 may supply fluid to the passageway 206. More specifically, the distal end portion 263 of each of the inboard injector ports and the outboard injector ports protrude through the first internal surface 214 and the second internal surface 216 such that fluid may be deposited into the passageway 206. Fluid may be transported from the proximal end portion 261 of the injector ports to the distal end portion 263 of the injector ports. Each of the injector ports may be shaped such that the injector port converges or diverges at the distal end portion 263. Thus, the cross sectional area of the proximal end portion 261 of the injector port may be greater than, less than, or equal to the cross sectional area of the distal end portion 263 of the injector port. For example, in some embodiments, the proximal end portion 261 of the injector port may have a larger cross sectional area than the distal end portion 263 of the injector port. Thus, the injector port may converge at the distal end portion 263 of the injector port to increase the velocity of the fluid being supplied to the passageway.

Each of the outboard injector ports 262 and the inboard injector ports 260 may extend from the outboard supply port and the inboard supply port, respectively, into the passageway 206 at a vertical injector angle $\alpha$. The vertical injector angle $\alpha$ may be from about 90 degrees to about 10 degrees and/or from about 75 degrees to about 15 degree and/or from about 60 degrees to about 30 degrees and/or from about 55 degrees to about 40 degrees with respect to at least one of the first internal surface 214 and the second internal surface 218. It is to be appreciated that the vertical injector angle $\alpha$ of any one injector port may be different than or the same as the vertical injector angle $\alpha$ of any other injector port. For example, a first injector port may have a vertical injector angle $\alpha$ of about 90 degrees with respect to at least one of the first internal surface 212 and the second internal surface 216 and a second injector port may have a vertical injector angle $\alpha$ of about 45 degrees with respect to at least one of the first internal surface 212 and the second internal surface 216.

Each of the outboard injector ports 262 and the inboard injector ports 260 may extend from the outboard supply port and the inboard supply port, respectively, into the passageway 206 at a horizontal injector angle $\theta$. The horizontal injector angle $\theta$ may be from 0 degrees to about 80 degrees and/or from about 0 degrees to about 60 degree and/or from about 0 degrees to about 30 degrees and/or from about 0 degrees to about 15 degrees with respect to the central longitudinal axis 224. It is to be appreciated that the horizontal injector angle $\theta$ of any one injector port may be different than or the same as the horizontal injector angle $\theta$ of any other injector port. For example, a first injector port may have a horizontal injector angle of about 0 degrees with respect to the central longitudinal axis 224 and a second injector port may have a horizontal injector angle of about 15 degrees with respect to the central longitudinal axis 224. The horizontal injector angle and the vertical injector angle may be determined, in part, by the properties of the discrete substrate 240.

It is to be appreciated that the bottom plate 204 and the top plate 202 may be configured in the same manner. Thus, the aforementioned disclosure may be applicable to both the bottom plate 204 and the top plate 202 of the transfer apparatus 200.

Referring to FIG. 7, the top plate 202 may include an inboard supply port and an outboard supply port. More specifically, the top plate 202 may include a first upper inboard supply port 264, a second upper inboard supply port 266, and a third upper inboard supply port 268. Each of the first upper inboard supply port 264, the second upper inboard supply port 266 and the third upper inboard supply port 268 may be spaced along the central longitudinal axis 224. The first upper inboard supply port 266 may be substantially in line with the inboard supply port 228 of the bottom plate 204. Similarly, the second upper inboard supply port 266 and the third upper inboard supply port 268 may be substantially in line with the second inboard supply port 232 and the third inboard supply port 236, respectively, of the bottom plate 204. It is to be appreciated that the upper inboard supply ports and the inboard supply ports do not have to be in line. However, it is believed that positing the inboard supply ports and the upper inboard supply ports in line with one another aids in advancing the discrete substrate within the passageway.

In some embodiments, at least one of the top plate 202 and the bottom plate 204 may be apportioned into zones. As illustrated in FIG. 7, each of the top plate 202 and the bottom plate 204 may be apportioned into a first zone 270, a second zone 272 adjacent to the first zone 270, and a third zone 274 adjacent to the second zone 272. Each zone may include one or more supply ports. In some embodiments, the first zone 270 of the top plate 202 and the bottom plate 204 may include a first upper inboard supply port 264 and a first inboard supply port 228, respectively. Similarly, the second zone 272 of the top plate 202 and the bottom plate 204 may include a second upper inboard supply port 266 and a second inboard supply port 232, respectively. Further, the third zone 274 of the top plate 202 and the bottom plate 204 may include a third upper inboard supply port 268 and a third inboard supply port 236, respectively. It is to be appreciated that the first zone 270, the second zone 272, and the third zone 274 may also include any number of outboard supply ports. It is to be appreciated that any number of zones may be used based on the plate length PL and the discrete substrate that is to be transported through the passageway.

As previously discussed, each of the supply ports may be fluidly connected to a control valve. More specifically, the first inboard supply port 228 may be fluidly connected to a first inboard control valve 248, the second inboard supply port 232 may be fluidly connected to a second inboard control valve 250, and the third inboard supply port 236 may be fluidly connected to the third inboard control valve 252. As illustrated in FIG. 7, the supply ports disposed on the top plate 202 may also be fluidly connected to a control valve. More specifically, the first upper inboard supply port 264 may be fluidly connected to the first inboard control valve 248, the second upper inboard supply port 250 may be fluidly connected to the second inboard control valve 250, and the third upper inboard supply port 268 may be fluidly connected to the third inboard control valve 252. Thus, the inboard control valves 252, 250, 248 may control the release and discontinue the release of fluid to the upper inboard supply ports and the inboard supply ports of the top plate 202 and the bottom plate 204, respectively.

It is to be appreciated that a separate set of control valves may control the first, second, and third, inboard upper supply ports. It is also to be appreciated that this same configuration may be used for the outboard supply ports. An outboard supply port of the top plate 202 and an outboard supply port of the bottom plate 204 may be controlled by the same outboard control valve, or each outboard supply port of the top plate 202 and each outboard supply port of the bottom plate 204 may be controlled by different outboard control valves.

In some embodiments, an individual control valve may be used to control the one or more supply ports present in each zone. More specifically, a first control valve may be used to control all the supply ports positioned in zone one, a second control valve may be used to control all the supply ports positioned in zone two, and a third control valve may be used to control all the supply ports positioned in zone three. It is also to be appreciated that in some other embodiments, more than one control valve may be used to control the one or more supply ports positioned in each zone. More specifically, for example, a first and second control valve may be used to control a first and second supply port positioned in the first zone, and a third, fourth, and fifth control valve may be used to control a third, fourth, and fifth supply port positioned in the second zone. A single control valve may control one or more supply ports. The position of the supply ports and the number of control valves may be determined by the discrete substrate that is to be transported through the passageway.

Still referring to FIG. 7, the transfer apparatus 200 may also include a visual tracking device 276. The visual tracking device 276 may be positioned adjacent to at least one of the top plate 202 and the bottom plate 204 such that at least a portion of the first surface 278 or the second surface 280 may be detectable by the visual detection device 276. The first surface 278 and the second surface 280 may be in facing relationship with at least one of the first internal surface 214 and the second internal surface 216. The visual detection device 276 may include a camera such as that disclosed in U.S. Patent Application entitled, "Systems and Methods for Monitoring and Controlling an Absorbent Article Converting Line," filed on Jun. 26, 2014, and identified by 62/017, 292. The visual detection device 276 may detect a portion of at least one of the leading edge portion 242, the trailing edge portion 244, the first edge portion 282, and the second edge portion 284 of the discrete substrate 240 as it moves through the passageway 206. By detecting at least a portion of the discrete substrate 240, the visual detection device 276 may be able to communicate the position of the discrete substrate 240.

In some embodiments, a portion of at least one of the top plate 202 and the bottom plate 204 may be made from a substantially transparent material such that the visual detection device 276 may detect at least a portion of the discrete substrate 240. For example, as illustrated in FIG. 5, the top plate 202 may include a transparent portion 334 and an opaque portion 336. The visual detection device 276 may be able to detect a portion of the discrete substrate 240 through the transparent portion 334 of the top plate 202. It is to be appreciated the transparent portion 334 may be any portion of the top plate 202 or the bottom plate 204 that allows the visual detection device 276 to communicate the position of the discrete substrate 240.

As illustrated in FIG. 8, the position of the discrete substrate 240 that may be gathered by the visual detection device 276 may be communicated to a controller 286. The controller 286 may be a programmable device that receives and analyzes the output from the visual detection device 276. The controller 286 may determine whether the position and velocity of the discrete substrate 240 is correct or needs to be modified. Stated another way, the controller 286 may be used to correct the position and the velocity of the discrete substrate 240 such that the discrete substrate 240 may be in a desired position and moving at a desired velocity. In some embodiments, the controller 286 may be a field-programmable gate array. It is to be appreciated that other controllers such as application specific integrated circuits or complex programmable logic devices may also be used.

The controller 286 may operate on a certain frequency. For example, the frequency may be at least 1 kHz. In some embodiments, where the controller is a field-programmable gate array, the field-programmable gate array may operate at a frequency of about 50 MHz. However, as will be discussed in more detail herein, the frequency at which the controller 286 operates may be limited to the frequency of the device to which the controller is communicating.

Based on the computations of the controller 286, the controller 286 communicates with at least one control valve 288. The discussion of the control valve 288 may apply to any of the aforementioned inboard and outboard control valves as previously discussed. The control valve 288 operates on a valve frequency. The valve frequency relates to how many times the control valve 288 can cycle on and off over a certain period of time. Thus, the valve frequency defines the total on-period and an off-period. The control valve 288 may have a valve frequency of at least about 100 Hz or at least about 200 Hz or at least about 300 Hz or at least about 400 Hz or at least about 500 Hz. Generally, the higher the valve frequency, the greater control over the control valve 288.

For example, in some embodiments, the control valve 288 may have a valve frequency of about 500 Hz. Thus, the control valves having a control frequency equal to about 500 Hz may complete one on/off cycle in about 0.002 sec. One on/off cycle includes an on-period and an off-period. An on-period refers to the amount of time in which fluid is being supplied to the supply port. An off-period refers to the amount of time in which fluid is not being supplied to the supply port. A control valve having a valve frequency of 500 Hz must complete an on-period and an off-period within about 0.002 sec. The controller 286 may control the duration of the on-period and the off-period for each cycle for each control valve 288. Thus, the controller 286 has the opportunity to change the on-period and the off-period every 0.002 sec, which allows the controller 286 to correct the position and the velocity of the discrete substrate 240 every 0.002 sec. For example, for each cycle, the controller 286 may determine the position and velocity of the discrete substrate. If the controller determines the position and/or the velocity of the discrete substrate 240 needs to be modified, the controller 286 may change the on-period and/or the off-period of the cycle of the control valve 288.

Figure 9A:
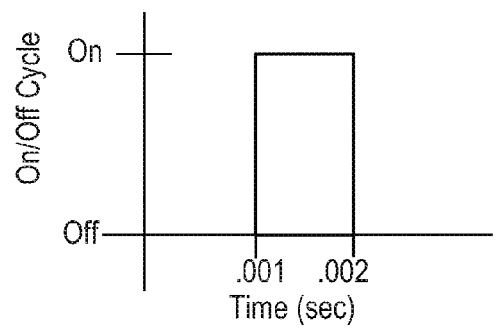
FIG. 9A is a graph of an on/off cycle for a control valve of a transfer apparatus in accordance with one non-limiting embodiment of the present disclosure.
Figure 9B:
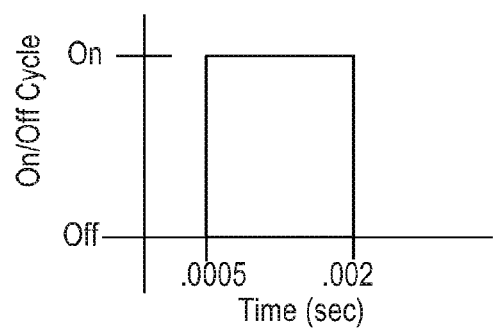
FIG. 9B is a graph of an on/off cycle for a control valve of a transfer apparatus in accordance with one non-limiting embodiment of the present disclosure.
Figure 9C:
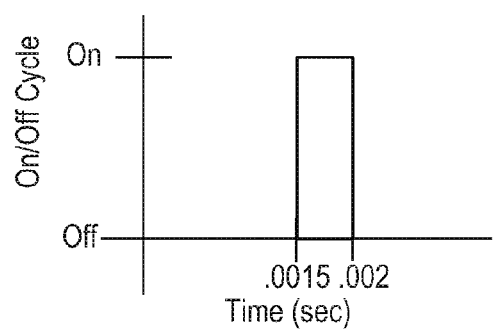
FIG. 9C is a graph of an on/off cycle for a control valve of a transfer apparatus in accordance with one non-limiting embodiment of the present disclosure.

FIGS. 9A-9C are each a graph of a cycle of the control valve 288. As illustrated in FIG. 9A, the cycle may be such that the control valve 288 may have an off-period equal to 0.001 seconds, or half the period of time in a cycle, and an on-period for 0.001 seconds, or half the period of time in a cycle. Once this first cycle is complete, the controller 286 may conclude, based on the position and velocity of the discrete substrate 240, which may be supplied by the visual detection device 276, to modify the on-period and the off-period of the subsequent cycle. As illustrated in FIGS. 9B and 9C, the controller 286 may indicate that the control valve 288 needs to have a longer on-period, or that the control valve 288 needs to have a longer off-period. By changing the on/off cycle of the control valve 288 the position and the velocity of the discrete substrate 240 may be adjusted.

Which control valve the controller 286 communicates with may be based on the position of the discrete substrate 240 within the passageway 206. Referring back to FIG. 7, as previously discussed, the transfer apparatus 200 may include a top plate 202 and a bottom plate 204 that each include a supply port including an injector port. In one embodiment, as the discrete substrate 240 enters the entry portion 208, the controller 286 may send an output to each of the control valves. The output may cause each of the control valves to become active. An active control valve may include any control valve with which the controller is communicating. Stated another way, each of the control valves may allow fluid to be supplied to the supply ports through the injector ports and into the passageway. Having each of the control valves become active may create the desired fluid flow within the passageway 206. The discrete substrate 240 may enter the entry portion 208 of the passageway 206 with an initial velocity, also referred to as a first velocity.

As the discrete substrate 240 advances in the machine direction MD through the passageway 206, the discrete substrate 240 will pass each inboard and outboard supply port. More specifically, as the discrete substrate 240 advances in the machine direction MD, the discrete substrate 240 may first encounter the fluid supplied by the first upper inboard supply port 264, the first upper outboard supply port (not shown), the first inboard supply port 228, and the first outboard supply port 230, as shown in FIGS. 6 and 7. The fluid supplied by this first set of inboard and outboard supply ports may engage the leading edge portion 242 of the discrete substrate 240, which causes the discrete substrate 240 to continue to advance in the machine direction MD. The leading edge portion 242 of the discrete substrate 240 may advance such that a second set of inboard and outboard supply ports and injector ports may cause fluid to engage the discrete substrate 240. More specifically, the second upper inboard supply port 266, the second upper outboard supply port (not shown), the second inboard supply port 232, and the second outboard supply port 234 route fluid into their respective injector ports and into the passageway. This fluid engages the leading edge portion 242 of the discrete substrate 240. As the fluid supplied by the second set of inboard and outboard supply ports and injector ports engages the leading edge portion 242 of the discrete substrate 240, the first set of inboard and outboard supply ports and injector ports may engage a central portion 290, which is between the leading edge portion 242 and the trailing edge portion 244, or the trailing edge portion 244 of the discrete substrate 240. Once either the central portion 290 or the trailing edge portion 244 passes the first set of supply ports and injector ports, the controller 286 may send output to the control valve(s) that control the first set of supply ports and injector ports. The output may cause the control valve(s) to become inactive. Thus, the first set of supply ports and injector ports no longer provide a fluid to the passageway. Stated another way, the control valve closes such that fluid may no longer be supplied to the first set of inboard and outboard supply ports. The controller may no longer communicate with the first inboard and outboard control valves while the discrete substrate continues to advance toward the exit portion of the passageway or until another discrete substrate enters the entry portion of the passageway. In some embodiments, the control valve may be in an inactive state because the controller continually communicates that the off period should span the entire duration of the cycle. The duty cycle of a control valve while inactive may be zero.

Similar to the above, the leading edge portion 242 of the discrete substrate 240 may advance in the machine direction MD toward the third set of inboard and outboard supply ports and injector ports. The third upper inboard supply port 268, the third upper outboard supply port (not shown), the third inboard supply port 236, and the third outboard supply port 238 may discharge fluid through their respective injector ports and into the passageway 206. The fluid may engage the leading edge portion 242 of the discrete substrate 240 causing the discrete substrate 240 to advance in the machine direction MD. The second set of inboard and outboard supply ports and injector ports may engage the central portion 290 and/or the trailing edge portion 244 with fluid. Once at least one of the central portion 290 and the trailing edge portion 244 advances past the second set of inboard and outboard supply ports and injector ports, the controller 286 may output to the control valve that controls second set of inboard and outboard supply ports and injector ports. The output causes the control valve to become inactive and the second set of inboard and outboard supply ports and injector ports may no longer supply fluid to the passageway 206. The controller may no longer communicate with the second inboard and outboard control valves while the discrete substrate continues to advance toward the exit portion of the passageway or until another discrete substrate enters the entry portion of the passageway.

In summary, each control valve may be active for at least a product period. The product period refers to the time for the leading edge portion of the discrete substrate to advance from a first set of supply ports to a second set of supply ports.

The discrete substrate 240 may advance to the exit portion 210 of the passageway 206. At the exit portion 210, the discrete substrate 240 may have a final velocity. The final velocity may be the velocity of an advancing substrate onto which the discrete substrate may be disposed. The final velocity may be greater than or equal to the initial velocity. The controller 286 ensures that the discrete substrate 240 has reached the final velocity or the velocity of the advancing substrate onto which the discrete substrate may be disposed. The controller 286 ensures that this final velocity is reached by communicating with each of the control valves. The controller 286 controls whether the control valve is active or inactive and the on/off cycle of each control valve. Stated another way, the controller 286 controls the period in which fluid is supplied into the passageway, the on-period of each cycle, and the period in which no fluid is supplied to the passageway, the off-period of each cycle. The average percentage of time that the control valve is on, the on-period, during each cycle while the control valve is active is referred to herein as the duty cycle. For example, a control valve may have a range of about 10% to about 90% duty cycle.

The controller 286 may also correct the position of the discrete substrate 240 such that when the discrete substrate 240 reaches the exit portion 210 of the passageway 206, the discrete substrate 240 may be in the desired position to be disposed on an advancing substrate. The controller 286 may change the position of the discrete substrate 240 by modifying the on/off cycle of the control valve and/or by changing whether the control valve remains active. For example, a discrete substrate 240 having additional material 292 attached thereto, as shown in FIG. 6, may require each of the inboard control valves and the outboard control valves to have different on/off cycles. More specifically, a discrete substrate 240 including additional material 292 may be imbalanced and, thus, may have a tendency to rotate due to the added weight of the additional material 292. Therefore, to prevent the discrete substrate 240 from rotating or to keep the discrete substrate 204 in the desired position, the fluid supplied to the passageway 206 may have to be supplied differently across the width W, which may be perpendicular to the machine direction MD, of the discrete substrate 240 and the length, which may be parallel to the machine direction, of the discrete substrate 240. The discrete substrate 240 may maintain a desired position in both the machine direction MD and the cross direction CD. The controller 286 allows the on/off cycles to be modified to account for a non-uniform discrete substrate 240.

As illustrated in FIG. 8, it is to be appreciated that the controller 286 may output the position and velocity to an external display device 294. Manufacturers may use the external display device to observe how the transfer apparatus 200 is operating.

Figure 10A:
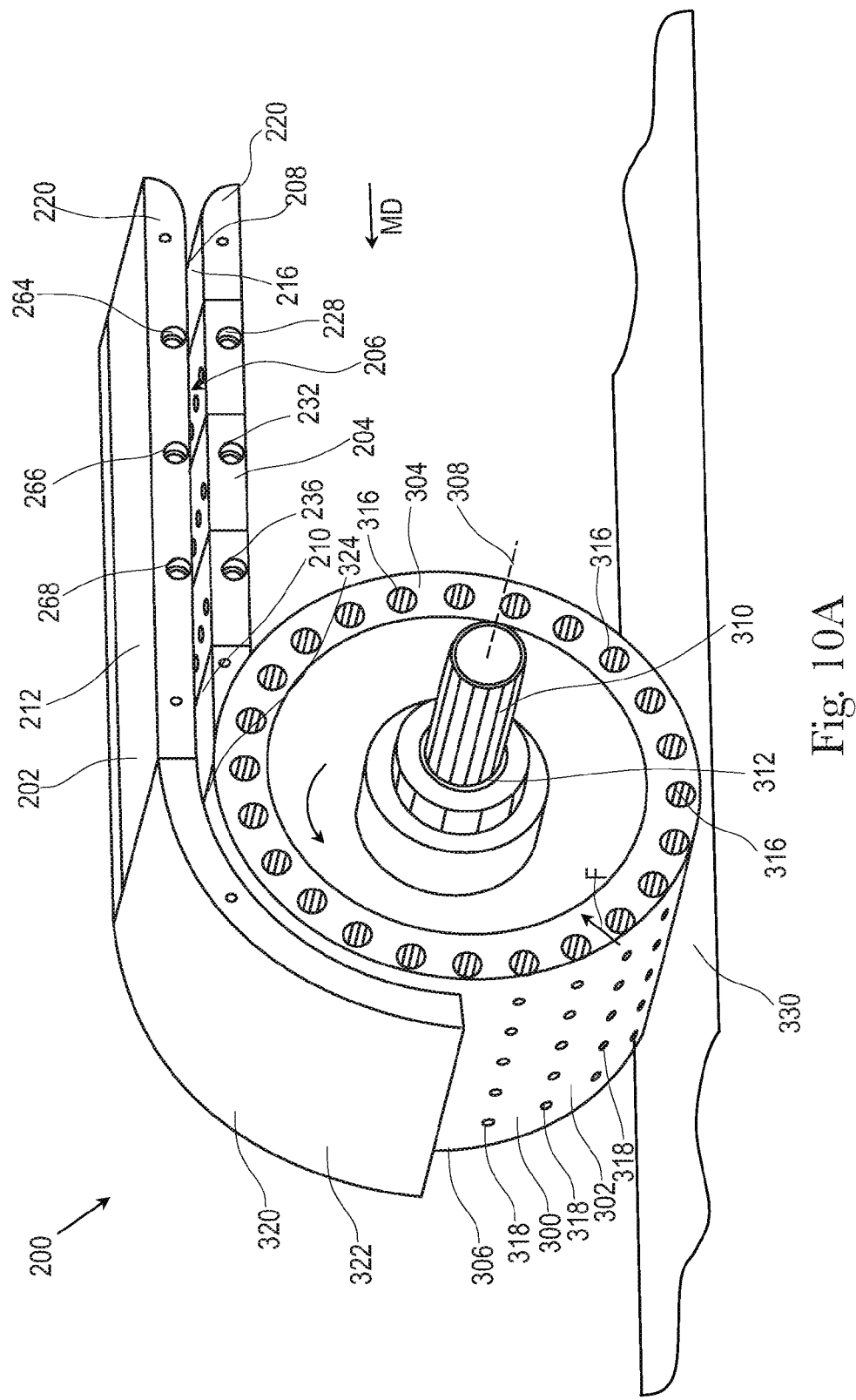
FIG. 10A is a perspective view of a transfer apparatus in accordance with one non-limiting embodiment of the present disclosure.

In some embodiments, as illustrated in FIGS. 10A and 10B, the transfer apparatus 200 may include a drum 300 operatively connected to the exit portion 210 of the passageway 206. The drum 300 may be used to adjust the velocity of the discrete substrate 240 as it leaves the exit portion 210 of the passageway 206. The drum 300 may accelerate or decelerate the discrete substrate 240 such that the velocity of the discrete substrate 240 may substantially match the velocity of the advancing substrate 330. The drum 300 may also be used to correct the position of the discrete substrate 240 with respect to the advancing substrate 330. The discrete substrate 240 may be required to be disposed at a certain position on the advancing substrate 330. Thus, the drum 300 may be used to accelerate and/or decelerate the discrete substrate 240 so that it may be disposed on the advancing substrate 330 at a desired position.

The drum 300 may be configured to rotate about a central longitudinal drum axis 308. The central longitudinal drum axis 308 may extend in a direction substantially perpendicular to the machine direction MD. In some embodiments, a shaft 310 may extend through the central region 312 of the drum 300. The shaft 310 may be driven by a drive mechanism 314, such as a motor, as illustrated in FIG. 10B. The drive mechanism 314 may be operatively connected to the shaft 310 such that the drive mechanism rotates the shaft 310. The shaft 310 operatively engages the drum 300 such that the shaft 310 and the drum 300 rotate about the central longitudinal drum axis 308.

Still referring to FIGS. 10A and 10B, the drum 300 may include an outer circumferential surface 302 extending between a first drum surface 304 and a second drum surface 306. At least one of the first drum surface 304 and the second drum surface 306 may include a vacuum port 316. The vacuum port 316 may be fluidly connected to one or more apertures 318 defined by the outer circumferential surface 302. The vacuum port 316 may also be fluidly connected to a vacuum source (not shown). The vacuum source may draw fluid through the apertures 318 and, subsequently, through the vacuum port 316 and back to the vacuum source. Drawing fluid through the apertures 318 may provide a force F to act on at least a portion of at least one of the first surface 278 and the second surface 280 of the discrete substrate 240. The force F may cause at least one of the first surface 278 and the second surface 280 to maintain contact with the outer circumferential surface 302 of the drum 300 during rotation. It is to be appreciated that the vacuum source may be controlled such that the discrete substrate 240 may be transferred from the drum 300 and onto the advancing substrate 330. It is also to be appreciated that force F created by each aperture 318 may be controlled individually. More specifically, a first portion of apertures 318 may be engaged such that the first portion of apertures 318 provide a force F on a discrete substrate 240, which may hold the discrete substrate to the outer circumferential surface 302. Simultaneously, a second portion of apertures 318 may be disengaged such that the second portion of apertures 318 fails to provide a force F on the discrete substrate 240, which may allow the discrete substrate to separate from the outer circumferential surface 302 of the drum 300.

In some embodiments, the transfer apparatus 200 may include a hood 320. The hood 320 may extend from the at least a portion of the top plate 202. The hood 320 may be positioned adjacent to the outer circumferential surface 302 of the drum 300. The hood 320 may have the same radius of curvature as the drum 300. The hood 320 may be used to help guide the discrete substrate from the exit portion 210 of the passageway 206 and onto to the outer circumferential surface 302 of the drum 300. The hood 320 may include an exterior hood surface 322 and an interior hood surface 324. The interior hood surface 324 may be in facing relationship with the outer circumferential surface 302 of the drum 300. The hood 320 may be made from a material such that the discrete substrate 240 may be visible from the exterior hood surface 324. For example, the hood 320 may be made from a transparent polymer material. It is to be appreciated that the hood 320 is not necessary to direct the discrete substrate from the passageway 206 and onto the drum 300.

Figure 11:
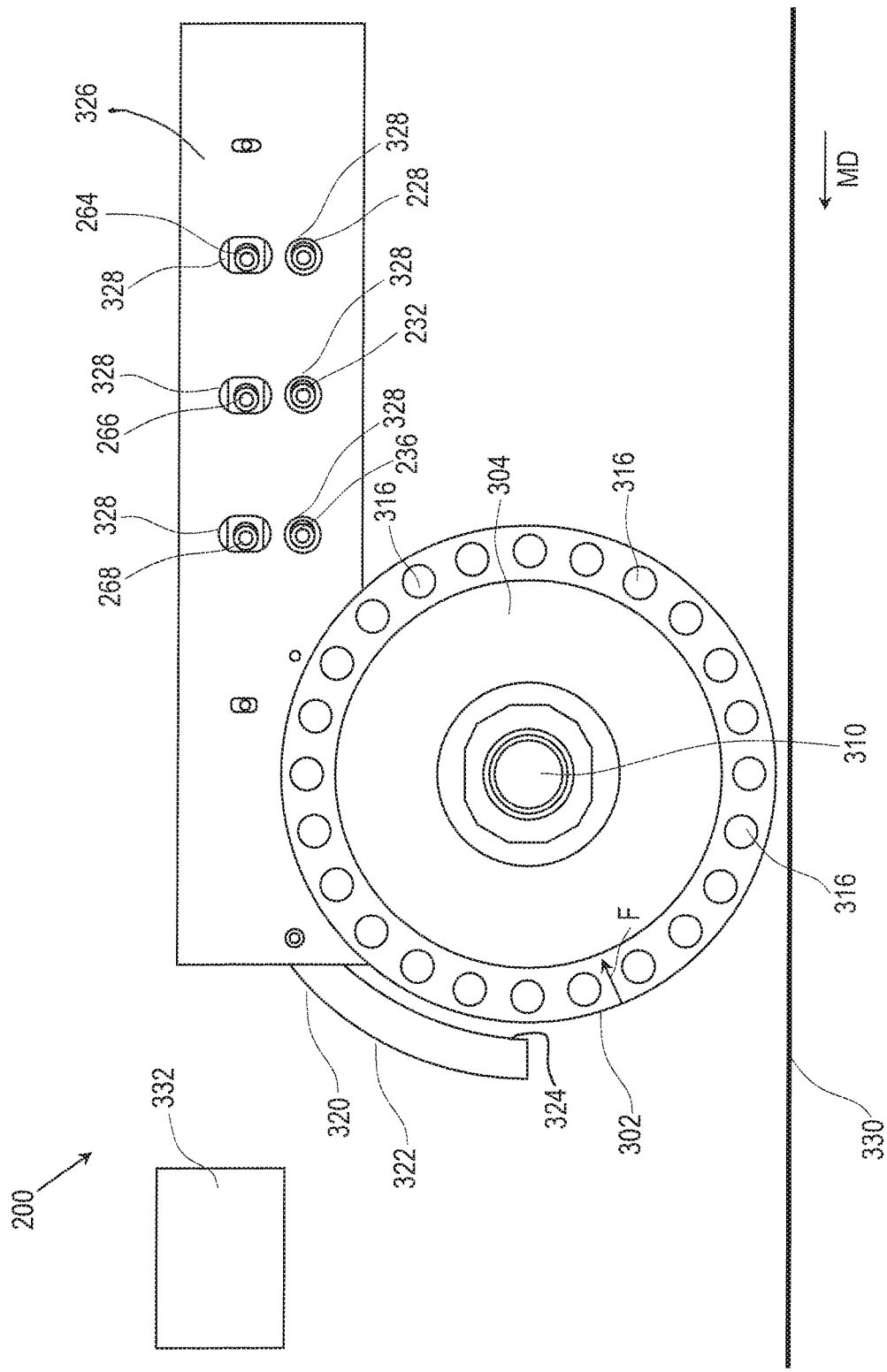
FIG. 11 is a side view of a transfer apparatus in accordance with one non-limiting embodiment of the present disclosure.

As illustrated in FIG. 11, the transfer apparatus 200 may include a first side plate 326 and a second side plate. The first side plate 326 and the bottom plate may be attached to at least one of the top plate 204 and the bottom plate 204. More specifically, the first side plate 326 may be attached to the inboard supply surface 220 of at least one of the top plate 202 and the bottom plate 204. The second side plate may be attached to the outboard supply surface 222 of at least one of the top plate 202 and the bottom plate 204. Each of the first side plate 326 and the second side plate may be substantially perpendicular to at least one of the top plate 202 and the bottom plate. Each of the first side plate and the second side plate may include one or more slots 328. The slots 328 may be positioned in the first side plate and the second side plate to allow access to each of the inboard and outboard supply ports. Each of the slots 328 may substantially surround the inboard or outboard supply ports.

In some embodiments, it is to be appreciated that fluid may be injected substantially perpendicular to the machine direction into the passageway in place of or in addition to the side plates. The fluid and/or side plates aid in directing the discrete substrate toward the exit portion of the passageway.

The transfer apparatus 200 may include a second visual detection device 332. The second visual detection device 332 may be positioned adjacent to the outer circumferential surface 302 of the drum 300. The visual detection device 332 may be positioned such that it may visually detect the velocity and position of the discrete substrate 240 as the discrete substrate leaves the exit portion 210 of the passageway 206. The visual detection device 332 may be a camera such as that disclosed in U.S. Patent Application entitled, "Systems and Methods for Monitoring and Controlling an Absorbent Article Converting Line," filed on Jun. 26, 2014, and identified by 62/017,292.

Figure 12B:
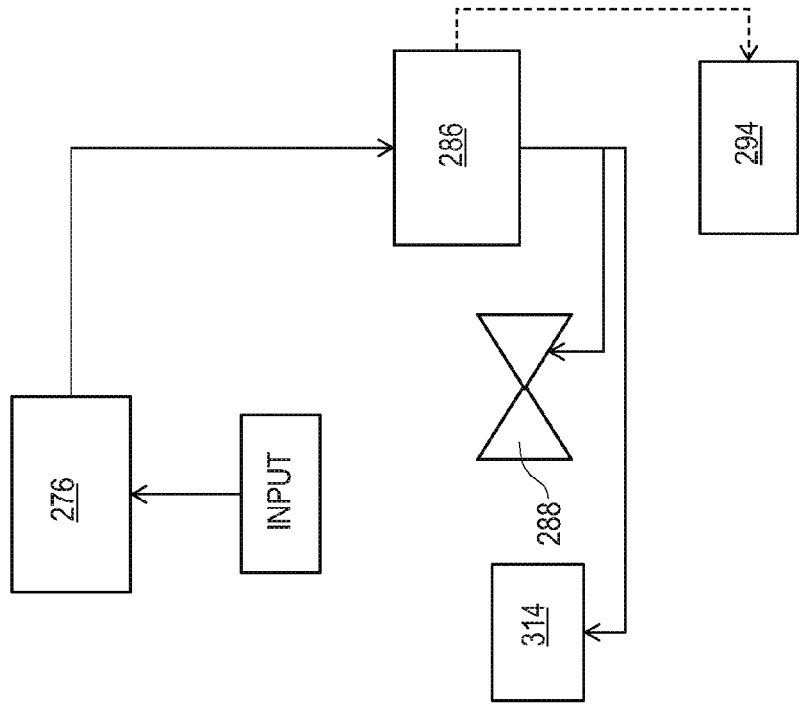
FIG. 12B is a schematic representation of communication between elements of a transfer apparatus in accordance with one non-limiting embodiment of the present disclosure.
Figure 12A:
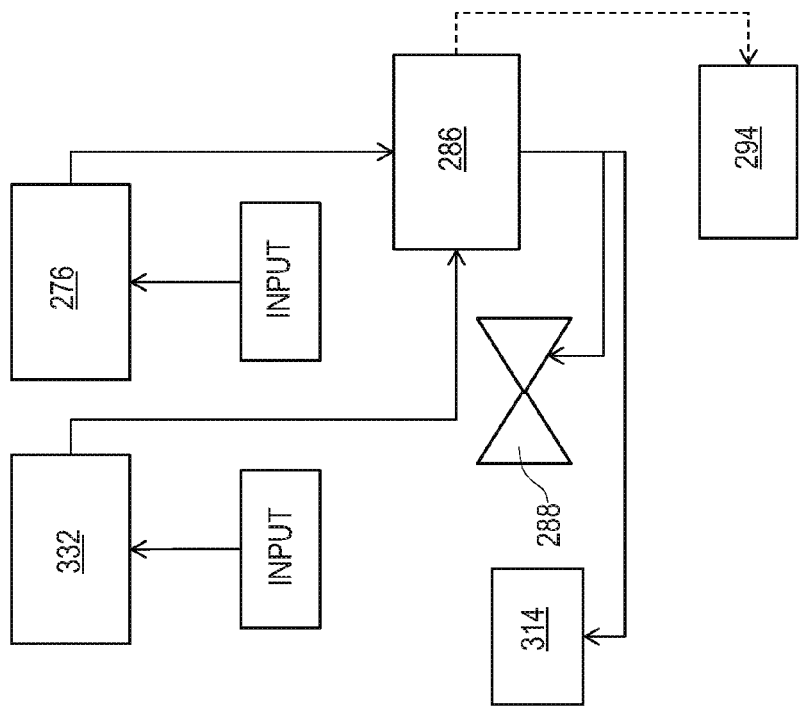
FIG. 12A is a schematic representation of communication between elements of a transfer apparatus in accordance with one non-limiting embodiment of the present disclosure.

The visual detection device 332 gathers the velocity and position of the discrete substrate 240, which is illustrated as input, and communicates this input to the controller 286, as illustrated in FIG. 12A. The controller 286 analyzes the input received from the second visual detection device 332. The controller 286 will then compute how the drum 300 should react to such input. The controller 286 then passes how the drum 300 should operate to the drive mechanism 314. The drive mechanism 314 may result in the drum 300 accelerating, decelerating, or maintaining the velocity and position of the discrete substrate 240. It is to be appreciated that the visual detection device 332 may communicate the information regarding the velocity and position of the discrete substrate to a second controller, different from the controller 286. The second controller would then communicate with the drum 300 as previously described.

In some embodiments, as illustrated in FIG. 12B, the visual detection device 276, as previously discussed, may be used to gather the velocity and position of the discrete substrate 240 as the discrete substrate leaves the exit portion 210 of the passageway 206. The visual detection device 276 may pass the velocity and position of the discrete substrate 240 to the controller 286. The controller 286 then analyzes this input and determines how the drum 300 should rotate such that the discrete substrate 240 may be disposed on the advancing substrate 330 with the desired velocity and in the desired position.

In view of the aforementioned, a method for transferring a discrete substrate may include the following steps. A transfer apparatus 200, as previously discussed, may be provided. The transfer apparatus may include a top plate and a bottom plate opposite the top plate. The top plate and the bottom plate may each include a first inboard supply port, and a first outboard supply port adjacent to the first inboard supply port. The top plate and the bottom plate may be positioned to define a passageway having an entry portion, an exit portion opposite the entry portion, and a central longitudinal axis extending in a machine direction. A discrete substrate may be fed into the passageway. The discrete substrate may include a leading edge portion, a trailing edge portion opposite the leading edge portion, and a central portion between the leading edge portion and the trailing edge portion. The discrete substrate may also include a first surface and a second surface opposite the first surface. The first surface may be in facing relationship with the top plate and the second surface may be in facing relationship with the bottom plate.

The discrete substrate may enter through the entry portion of the passageway at a first velocity and may exit through the exit portion of the passageway at a final velocity. The final velocity may be greater than or equal to the first velocity, also referred to herein as the initial velocity.

A first inboard control valve may be engaged to supply fluid to the first inboard supply port. A first outboard control valve may be engaged to supply fluid to the first outboard supply port. A controller may be operatively connected to the first inboard control valve and the first outboard control valve. The controller may be used to control whether each of the first inboard control valve and the first outboard control valve are active or inactive and to control the on/off cycle. By using the controller to control whether the control valves are active and inactive and to modify and/or maintain the on/off period for each cycle, the discrete substrate may be adjusted as it is advanced in the machine direction.

The controller may use input from a visual detection device. The visual detection device may track at least a portion of the discrete substrate. The visual detection device may be positioned adjacent to at least one of the top plate and the bottom plate such that at least a portion of at least one of the first surface and the second surface of the discrete substrate may be detectable by the visual detection device.

In some embodiments, the discrete substrate may leave the exit portion of the passageway and may be disposed on a drum. The drum may rotate about a central longitudinal drum axis. The drum may deposit the discrete substrate on an advancing substrate at a desired velocity and in a desired position.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method for transferring a discrete substrate, the method comprising the steps of:
   providing a transfer apparatus comprising a top plate and a bottom plate opposite the top plate, wherein the top plate and the bottom plate include a first supply port, and a first outboard supply port adjacent to the first inboard supply port, and wherein the top plate and the bottom plate define a passageway having an entry portion, an exit portion opposite the entry portion, and a central longitudinal axis extending in a machine direction;
   feeding a discrete substrate comprising a leading edge portion, a trailing edge portion opposite the leading edge portion, a central portion between the leading edge portion and the trailing edge portion, a first surface, and a second surface opposite the first surface through the transfer apparatus, wherein the discrete substrate enters through the entry portion of the passageway at a first velocity and exits through the exit portion of the passageway at a final velocity, wherein the final velocity is greater than the first velocity;
   activating a first inboard control valve to supply fluid to the first inboard supply port;
   activating a first outboard control valve to supply fluid to the first outboard supply port, wherein the first inboard control valve and the first outboard control valve operate on a valve frequency, wherein the valve frequency defines an on-period and an off-period for each cycle;
   controlling each of the first inboard control valve and the first outboard control valve with a controller, wherein the controller modifies the on-period and the off-period for each cycle for each of the first inboard control valve and the first outboard control valve;
   advancing the discrete substrate in a machine direction;
   tracking at least a portion of the discrete substrate with a visual detection device, wherein the visual detection device is positioned adjacent to at least one of the top plate and the bottom plate such that at least a portion of at least one of the first surface and the second surface of the discrete substrate is detectable by the visual detection device; and
   adjusting the discrete substrate;
   wherein the first inboard supply port includes a plurality of inboard injector ports extending along the length of the first inboard supply port and the first outboard supply port includes a plurality of outboard injector ports extending along the length of the first outboard supply port, wherein each of the plurality of ports extend from at least one of the first inboard supply port and the first outboard supply port into the passageway.

2. The method of claim 1, wherein each of the first inboard control valve and the first outboard control valve are active for at least a product period.

3. The method of claim 2, wherein the step of controlling the first inboard control valve and the first outboard control valve includes activating and deactivating the first inboard control valve and the first outboard control valve.

4. The method of claim 1, wherein the step of modifying the on-period and the off-period for each cycle includes at least one of increasing and decreasing the on-period.

5. The method of claim 1, wherein the first inboard supply port and the first outboard supply port remain active while at least one of the first inboard supply port and the first outboard supply port engages the leading edge portion of the discrete substrate with fluid to when at least one of the first inboard supply port and the first outboard supply port engages at least one of the central portion and the trailing edge portion of the discrete substrate with fluid.

6. The method of claim 1, wherein the first inboard supply port is fluidly connected to a first inboard injector port and first outboard supply port is fluidly connected to a first outboard injector port.

7. The method of claim 6, wherein the fluid supplied to the first inboard supply port exits through the first inboard injector engaging at least a portion of the leading edge portion of the discrete substrate and advancing the discrete substrate toward the exit portion of the passageway.

8. The method of claim 6, wherein the fluid supplied to the first outboard supply port exits through the first outboard injector engaging at least a portion of the leading edge portion of the discrete substrate and advancing the discrete substrate toward the exit portion of the passageway.

9. The method of claim 1, wherein the controller is operatively connected to the visual detection device.

10. The method of claim 1, further comprising the step of inactivating the first inboard control valve to stop the supply of fluid to the first inboard supply port.

11. The method of claim 1, further comprising the step of inactivating the first outboard control valve to stop the supply of fluid to the first outboard supply port.

12. The method of claim 1, wherein at least one of the first inboard supply port and the first outboard supply port is substantially perpendicular to the central longitudinal axis of the passageway.

13. The method of claim 1, wherein the first outboard supply port is at a supply port angle with respect to the central longitudinal axis, wherein the supply port angle is from about 75 degrees to about 15 degrees.

14. The method of claim 1, wherein the first inboard supply port is at a supply port angle with respect to the central longitudinal axis, wherein the supply port angle is from about 75 degrees to about 15 degrees.

15. The method of claim 1, wherein each of the plurality of ports has a vertical injector angle with respect to an internal surface of at least one of the top plate and the bottom plate wherein the vertical injector angle is from about 15 degrees to about 75 degrees.

16. The method of claim 15, wherein the injector angle is from about 30 degrees to about 60 degrees.

17. The method of claim 15, wherein each of the plurality of ports has a horizontal injector angle with respect to the central longitudinal axis, wherein the horizontal injector angle is from about 0 degrees to about 30 degrees.

18. The method of claim 1, wherein the first surface of the discrete substrate is in facing relationship with the top plate and the second surface of the discrete substrate is in facing relationship with the bottom plate.

19. The method of claim 1, wherein each of the first inboard supply port and the first outboard supply port include an inlet portion and an end portion opposite the inlet portion, and wherein the fluid enters through the inlet portion and moves toward the end portion.

20. The method of claim 1, wherein the transfer apparatus comprises a first side plate substantially perpendicular to at least one of the top plate and the bottom plate, and a second side plate opposite the first side plate.

21. The method of claim 1, further comprising the steps of:
activating a second inboard control valve to supply fluid to a second inboard supply port; and
activating a second outboard control valve to supply fluid to a second outboard supply port.

22. The method of claim 1, wherein the visual detection device is a camera positioned along the machine direction.

23. The method of claim 1, wherein the controller comprises a field-programmable gate array.

24. The method of claim 1, wherein the discrete substrate is a nonwoven.

25. The method of claim 1, wherein the step of adjusting the discrete substrate includes modifying at least one of the longitudinal velocity and the angular velocity.

26. The method of claim 1, wherein the visual detection device communicates with the controller, and the controller modifies the on-period and the off-period for each cycle.

27. A method for transferring a discrete substrate, the method comprising the steps of:
providing a transfer apparatus comprising a top plate and a bottom plate opposite the top plate, wherein the top plate and the bottom plate include a first supply port, and a first outboard supply port adjacent to the first inboard supply port, and wherein the top plate and the bottom plate define a passageway having an entry portion, an exit portion opposite the entry portion, and a central longitudinal axis extending in a machine direction;
feeding a discrete substrate comprising a leading edge portion, a trailing edge portion opposite the leading edge portion, a central portion between the leading edge portion and the trailing edge portion, a first surface, and a second surface opposite the first surface through the transfer apparatus, wherein the discrete substrate enters through the entry portion of the passageway at a first velocity and exits through the exit portion of the passageway at a final velocity, wherein the final velocity is greater than the first velocity;
activating a first inboard control valve to supply fluid to the first inboard supply port;
activating a first outboard control valve to supply fluid to the first outboard supply port, wherein the first inboard control valve and the first outboard control valve operate on a valve frequency, wherein the valve frequency defines an on-period and an off-period for each cycle;
controlling each of the first inboard control valve and the first outboard control valve with a controller, wherein the controller modifies the on-period and the off-period for each cycle for each of the first inboard control valve and the first outboard control valve;
advancing the discrete substrate in a machine direction;
tracking at least a portion of the discrete substrate with a visual detection device, wherein the visual detection device is positioned adjacent to at least one of the top plate and the bottom plate such that at least a portion of at least one of the first surface and the second surface of the discrete substrate is detectable by the visual detection device;
adjusting the discrete substrate;
detecting the final velocity of the discrete substrate at the exit portion of the passageway;
adjusting the speed of a drum to accept the discrete substrate;
accepting the discrete substrate onto an outer circumferential surface of the drum;
at least one of accelerating and decelerating the drum to position the discrete substrate onto an advancing substrate, wherein the advancing substrate is moving in the machine direction.

28. The method of claim 27, wherein a second visual detection device is used to detect the final velocity and a final position of the discrete substrate.

29. The method of claim 27, wherein the visual detection device is used to detect the final velocity and a position of the discrete substrate.

30. An apparatus for transferring a discrete substrate, the apparatus comprising:
a transfer apparatus comprising a top plate and a bottom plate opposite the top plate, wherein the top plate and the bottom plate include a first inboard supply port, a first inboard injector port fluidly connected to the first inboard supply port, a first outboard supply port adjacent to the first inboard supply port, and a first outboard injector port fluidly connected to the first outboard supply port, and wherein the top plate and the bottom plate define a passageway having an entry portion and an exit portion;
a drum operatively connected to the exit portion of the passageway, wherein the drum rotates about a central longitudinal drum axis;
a first inboard control valve operatively connected to the first inboard supply port, wherein the first inboard control valve regulates a flow of a fluid to the first inboard supply port and the first inboard injector port;
a first outboard control valve operatively connected to the first outboard supply port, wherein the first outboard control valve regulates the flow of the fluid to the first outboard supply port and the first outboard injector port;
a visual detection device positioned adjacent to at least one of the top plate and the bottom plate such that at least a portion of at least one of a first surface and a second surface of a discrete substrate is detectable by the visual detection device; and
a controller operatively connected to the visual detection device and at least one of the first inboard control valve and the first outboard control valve, wherein the discrete substrate enters through the entry portion of the passageway at a first velocity, moves through the passageway in a machine direction, and exits through the exit portion of the passageway at a final velocity, and wherein the final velocity is greater than the first velocity.

31. The apparatus of claim 30, wherein the first inboard control valve and the first outboard control valve operate on a valve frequency, wherein valve frequency defines a first on period, a first off period, a second on period, and a second off period.

32. The apparatus of claim 31, wherein the first on period is at least one of greater than, less than, or equal to the second on period.

33. The apparatus of claim 30, wherein the top plate and the bottom plate comprise a second inboard supply port, a second inboard injector port fluidly connected to the second inboard supply port, a second outboard supply port adjacent to the second inboard supply port, and a second outboard injector port fluidly connected to the second outboard supply port.

34. The apparatus of claim 33, further comprising a second inboard control valve operatively connected to the second inboard supply port, wherein the second inboard control valve regulates the flow of the fluid to the second inboard supply port and the second inboard injector.

35. The apparatus of claim 33, further comprising a second outboard control valve operatively connected to the second outboard supply port, wherein the second outboard control valve regulates the flow of the fluid to the second outboard supply port and the second outboard injector.

36. The apparatus of claim 30, each of the first outboard injector port and the first inboard injector port have a vertical injector angle with respect to an interior surface of at least one of the top plate and the bottom plate, and each of the first outboard injector port and the first inboard injector port have a horizontal injector angle with respect to the central longitudinal axis.

37. The apparatus of claim 30, wherein the controller comprises a field-programmable gate array.

* * * * *